(12) United States Patent
Mariampillai et al.

(10) Patent No.: US 10,143,523 B2
(45) Date of Patent: Dec. 4, 2018

(54) SYSTEMS, METHODS AND DEVICES FOR TRACKING AND CALIBRATION OF FLEXIBLE INSTRUMENTS

(71) Applicant: 7D SURGICAL INC., Toronto, ON (CA)

(72) Inventors: Adrian Mariampillai, Toronto (CA); Peter Siegler, Toronto (CA); Michael Leung, Markham (CA); Beau Anthony Standish, Toronto (CA); Victor X. D. Yang, Toronto (CA)

(73) Assignee: 7D SURGICAL INC., Toronto, ON (CA)

( * ) Notice: Subject to any disclaimer, the term of this patent is extended or adjusted under 35 U.S.C. 154(b) by 0 days.

(21) Appl. No.: 15/562,249

(22) PCT Filed: Mar. 31, 2016

(86) PCT No.: PCT/CA2016/050374
§ 371 (c)(1),
(2) Date: Sep. 27, 2017

(87) PCT Pub. No.: WO2016/154756
PCT Pub. Date: Oct. 6, 2016

(65) Prior Publication Data
US 2018/0078317 A1 Mar. 22, 2018

Related U.S. Application Data

(60) Provisional application No. 62/140,884, filed on Mar. 31, 2015.

(51) Int. Cl.
*G02B 6/00* (2006.01)
*A61B 34/20* (2016.01)
(Continued)

(52) U.S. Cl.
CPC .... *A61B 34/20* (2016.02); *A61B 2017/00725* (2013.01); *A61B 2034/2055* (2016.02);
(Continued)

(58) Field of Classification Search
CPC ............ A61B 34/20; A61B 2034/2061; A61B 2034/2055; A61B 2017/00725; A61B 2090/3983
See application file for complete search history.

(56) References Cited

U.S. PATENT DOCUMENTS 5,946,094 A * 8/1999 Sahlgren ............... E21B 47/022
356/477
6,471,710 B1 10/2002 Bucholtz
(Continued)

OTHER PUBLICATIONS

Written Opinion for PCT/CA2016/050374 dated Jul. 5, 2016.
(Continued)

*Primary Examiner* — Ellen Kim
(74) *Attorney, Agent, or Firm* — Hill & Schumacher

(57) ABSTRACT

Systems, methods and devices are provided for calibrating a flexible implement that employs fiber Bragg gratings (FBGs) for shape sensing. In some embodiments, methods and devices are provided for determining the longitudinal location of a FBG within an optical fiber that is employed for shape sensing. In other embodiments, methods and devices are employed for the determination of calibration parameters that relate the measured wavelength shift of a set of FBGs to the curvature at the location within the flexible implement where the set of FBGs resides. Various calibration devices are disclosed that employ guiding features for bending the flexible portion of the flexible implement along known curved profiles. In some embodiments, keyed features are incorporated into the flexible implement and the calibration device, such that the flexible implement is inserted into the
(Continued)

device in a known orientation. In some embodiments, the flexible implement may incorporate a strain isolation mechanism.

12 Claims, 29 Drawing Sheets

(51) Int. Cl.
*A61B 17/00* (2006.01)
*A61B 90/00* (2016.01)

(52) U.S. Cl.
CPC .............. *A61B 2034/2061* (2016.02); *A61B 2090/3983* (2016.02)

(56) References Cited

U.S. PATENT DOCUMENTS

| | | | |
|---|---|---|---|
| 6,854,327 B2 | 2/2005 | Rambow et al. |
| 6,868,195 B2 | 3/2005 | Fujita |
| 7,194,296 B2 | 3/2007 | Frantz et al. |
| 8,183,520 B2 | 5/2012 | Prisco |
| 8,463,439 B2 | 6/2013 | Blumenkranz et al. |
| 8,649,847 B1 | 2/2014 | Park et al. |
| 8,818,143 B2 | 8/2014 | Younge et al. |
| 2006/0013523 A1 | 1/2006 | Childlers et al. |
| 2009/0137952 A1 | 5/2009 | Ramamurthy et al. |
| 2011/0224684 A1 | 9/2011 | Larkin et al. |
| 2013/0109957 A1 | 5/2013 | 'T Hooft et al. |
| 2013/0190734 A1 | 7/2013 | Taylor et al. |
| 2013/0245640 A1 | 9/2013 | Whitmore, III |
| 2014/0005465 A1 | 1/2014 | Ribbing |
| 2014/0114180 A1 | 4/2014 | Jain |

OTHER PUBLICATIONS

International Search Report for PCT/CA2016/050374 dated Jul. 5, 2016.
Multiplexed Force and Deflection Sensing Shell Membranes for Robotic Manipulators, NASA Tech Briefs, 2012.
Rajan et al., IEEE Sens. J. 10, 1913-1920 (2010).
MRI-compatible haptics: deflection and force sensing of biopsy needles and other tools using FBG sensors, https://web.archive.org/web/20150918230540/http://bdml.stanford.edu/twiki/bin/view/haptics/bendingsurgicaltool.html; 2015.
Park, IEEE/ASME Transactions on Mechatronics, 15, 906-915 (2010).
Park, International Society for Magnetic Resonance in Medicine (ISMRM), 2008.
Park, International Society for Magnetic Resonance in Medicine (ISMRM), 2009.
Taffoni et al., Sensors 13, 14105-14120 (2013).
Abushagur et al., Sensors 14, 6633-6665 (2014).

* cited by examiner 220　　　246

246

246

246

246

246

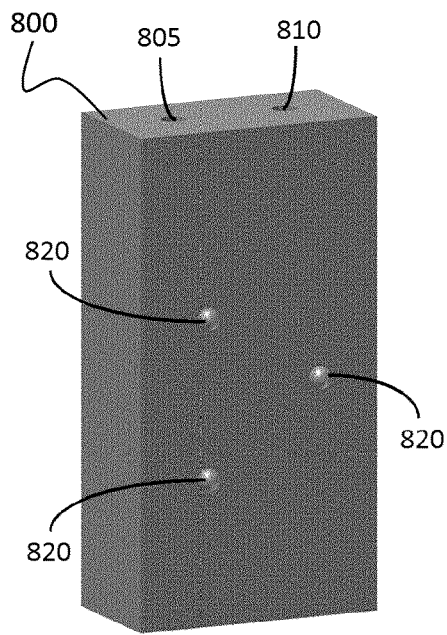
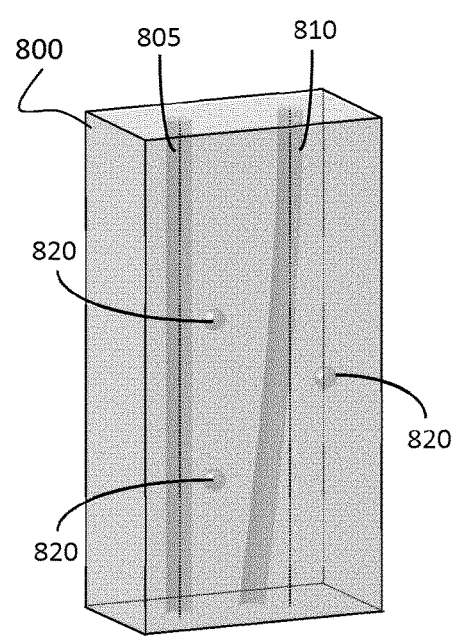
FIG. 18A　　　　　　　　　　FIG. 18B
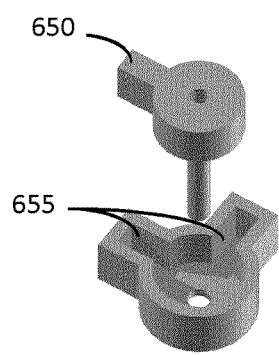
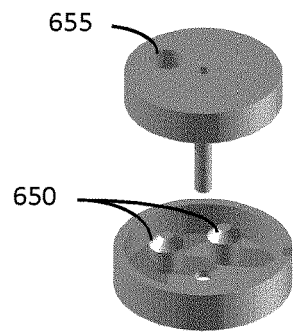
FIG. 18C　　　　　　　　　　FIG. 18D

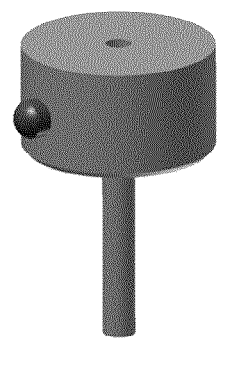
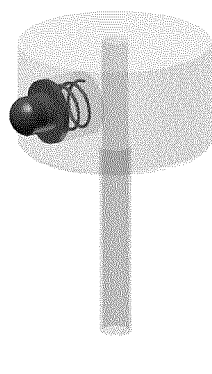
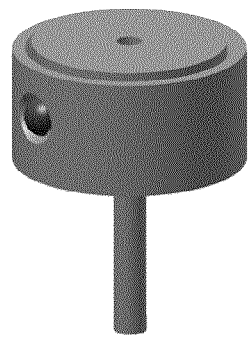
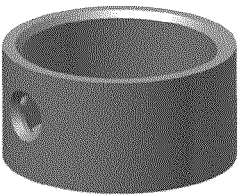
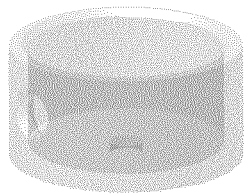
FIG. 19B     FIG. 19C     FIG. 19D

SYSTEMS, METHODS AND DEVICES FOR TRACKING AND CALIBRATION OF FLEXIBLE INSTRUMENTS

CROSS-REFERENCE TO RELATED APPLICATION

This application is a National Phase application claiming the benefit of the international PCT Patent Application No. PCT/CA2016/050374, filed on Mar. 31, 2016, in English, which claims priority to U.S. Provisional Application No. 62/140,884, titled "SYSTEMS, METHODS AND DEVICES FOR TRACKING AND CALIBRATION OF FLEXIBLE INSTRUMENTS" and filed on Mar. 31, 2015, the entire contents of which are incorporated herein by reference.

BACKGROUND

The present disclosure relates to guidance and tracking systems for tracking flexible implements, such as flexible medical instruments. More specifically, the present disclosure relates to an integrated system of markers (active or passive) and fiber Bragg grating (FBG) arrays arranged for interventional and/or surgical procedures and the tracking of flexible medical implements used in these procedures such as needles, catheters and endoscopes.

Surgical guidance enables surgeons to localize the position of rigid surgical instruments relative to the human body without having complete visual access during surgery. Surgical guidance is routinely used in surgeries that involve anatomical locations such as the spine, brain, hip, ear/nose/throat or other organs.

In general, surgical guidance consists of two steps: The first step includes the acquisition of a three dimensional (3D) data set of a relevant anatomical region of the body. This step may involve single or multiple imaging modalities such as computed tomography (CT), magnetic resonance tomography (MRT), positron emission tomography (PET) and ultrasound (US). The 3D data set may be acquired before and/or during the surgical procedure. In the second step, the spatial position of the body and the spatial relation of the surgical instruments to the position of the anatomical region are tracked during the surgery. The spatial position of this anatomical region is then correlated to its 3D data set using specific image registration techniques. After registration, the spatial position of the surgical instruments can be displayed with a 3D representation of the anatomical region for the surgeon.

Typically, optical-based systems are used for tracking spatial positions during the surgery. These systems are based on two cameras that detect the positions of at least three markers attached to the tracked rigid surgical instruments (for example, mounted with LEDs as disclosed in U.S. Pat. No. 5,921,992, or mounted with reflective probes as disclosed in U.S. Pat. No. 6,061,644).

Flexible medical implements are used in a wide variety of medical procedures such as endoscopy, angiography and biopsies to name a few. These medical procedures utilize flexible medical implements such as endoscopes, catheters and needles. These types of implements cannot be accurately tracked using the optical techniques described above due to the deflections they might experience during procedures.

A Fiber Bragg Grating (FBG) is a type of optical sensor, which can be constructed by exposing a photosensitive fiber to a spatially varying distribution of light to induce a periodic index of refraction change within the core of the fiber. When a broadband light source or a tunable laser is coupled into the waveguide, certain wavelengths will be reflected and transmitted based on the periodicity of the grating (Fresnel Reflection), where the reflected wavelength is known as the Bragg wavelength $\lambda_B$.

Applying strain ($\epsilon$) and a change in temperature $\Delta T$ to a FBG causes a relative shift of the corresponding Bragg wavelength ($\Delta\lambda_B/\lambda_B$), which is given by:

$$\left[\frac{\Delta\lambda_B}{\lambda_B}\right] = (1 - p_e)\epsilon + (\alpha_\Lambda + \alpha_n)\Delta T \quad (1)$$
$$= C_S\epsilon + C_T\Delta T$$

Here, $p_e$ is the strain optic coefficient, $\alpha_\Lambda$ the thermal expansion coefficient of the optical fiber and $\alpha_n$ the thermo-optic coefficient, which can be combined to linear coefficients for the strain $C_S$ and the temperature $C_T$.

Similarly the wavelength broadening $\Delta\lambda_{BW}$ is given by:

$$\Delta\lambda_{BW} = 2n_{eff}\Lambda(1-p_e)\Delta\epsilon \quad (2)$$

$$\Delta\epsilon = \epsilon_{max} - \epsilon_{min} \quad (3)$$

$\Delta\epsilon$ is the strain gradient across the length of the grating, $n_{eff}$ is the fiber core index of refraction and $\Lambda$ is the FBG periodicity.

However, it is much more common, to use the wavelength shift in a FBG to create highly sensitive temperature sensors and strain gauges for a variety of industrial and scientific applications. These measurements can be used to infer a local bending radius of curvature the FBG undergoes, yielding information about the shape of the fiber and/or a device to which it is securely attached.

SUMMARY

Systems, methods and devices are provided for calibrating a flexible implement that employs fiber Bragg gratings (FBGs) for shape sensing. In some embodiments, methods and devices are provided for determining the longitudinal location of a FBG within an optical fiber that is employed for shape sensing. In other embodiments, methods and devices are employed for the determination of calibration parameters that relate the measured wavelength shift of a set of FBGs to the curvature at the location within the flexible implement where the set of FBGs resides. Various calibration devices are disclosed that employ guiding features for bending the flexible portion of the flexible implement along known curved profiles. In some embodiments, keyed features are incorporated into the flexible implement and the calibration device, such that the flexible implement is inserted into the device in a known orientation. In some embodiments, the flexible implement may incorporate a strain relief mechanism.

Accordingly, in a first aspect, there is provided a method of determining a longitudinal location of a fiber Bragg grating within an optical fiber, wherein the optical fiber is attached to or housed within an elongate flexible implement, the method comprising:

recording an initial reflected optical wavelength of the fiber Bragg grating in the absence of bending of the elongate flexible implement;

bending the elongate flexible implement according to a first known curved profile and recording a first reflected optical wavelength shift of the fiber Bragg grating;

bending the elongate flexible implement according to a second known curved profile and recording a second reflected optical wavelength shift of the fiber Bragg grating, wherein the first known curved profile and the second known curved profile are configured to bend the elongate flexible implement along a common direction; and determining, as the longitudinal location of the fiber Bragg grating, a longitudinal distance for which a ratio of the curvature of the first known curved profile to the curvature of the second known curved profile equals a ratio of the first reflected optical wavelength shift to the second reflected optical wavelength shift.

In another aspect, there is provided a calibration apparatus for use in determining a longitudinal location of a fiber Bragg grating within an optical fiber, wherein the optical fiber is attached to or housed within an elongate flexible implement, the calibration apparatus comprising:

one or more first guiding features suitable for receiving the elongate flexible implement and bending the elongate flexible implement along a first known curved profile; and one or more second guiding features suitable for receiving the elongate flexible implement and bending the elongate flexible implement along a second known curved profile;

wherein said first and second guiding features are configured such that a ratio of the curvature of the first known curved profile to the curvature of the second known curved profile, as determined at a common longitudinal distance along each known curved profile, varies with longitudinal distance;

wherein said first and second guiding features are configured to bend the elongate flexible implement along a common direction; and wherein the first known curved profile and the second known curved profile are selected such that a dependence, on longitudinal distance, of the ratio of the curvature of the first known curved profile to the curvature of the second known curved profile, is single-valued.

In another aspect, there is provided a method of calibrating a relationship between wavelength shift and curvature for a shape-sensing elongate flexible implement, the shape-sensing elongate flexible implement comprising at least three optical fibers, wherein at least two optical fibers are offset from a longitudinal axis of the shape-sensing elongate flexible implement, wherein the at least three optical fibers are not mutually coplanar, wherein the optical fibers comprise a set of fiber Bragg gratings provided at a common longitudinal location within the shape-sensing elongate flexible implement, wherein each fiber Bragg grating of the set of fiber Bragg gratings is provided in a different optical fiber, the method comprising:

a) recording a reference reflected optical wavelength of each fiber Bragg grating when a flexible portion of the shape-sensing elongate flexible implement is provided in a reference configuration;

b) bending a flexible portion of the shape-sensing elongate flexible implement along a first direction relative to a reference frame associated with fiducial markers attached a rigid portion of the shape-sensing elongate flexible implement, such that the shape-sensing elongate flexible implement is bent according to a first known curved profile;

c) recording a first reflected optical wavelength shift of each fiber Bragg grating;

d) bending the flexible portion of the shape-sensing elongate flexible implement along a second direction relative to the reference frame associated with the fiducial markers attached to the rigid portion of the shape-sensing elongate flexible implement, such that the shape-sensing elongate flexible implement is bent according to a second known curved profile, wherein the first direction is different from the second direction;

e) recording a second reflected optical wavelength shift of each fiber Bragg grating;

f) determining a first curvature of first known profile and a second curvature of the second known curved profile, wherein the first curvature and the second curvature are determined at a longitudinal position of the set of fiber Bragg gratings; and g) processing the first reflected optical wavelength shifts and the second reflected optical wavelength shifts, and the first curvature and the second curvature of the shape-sensing elongate flexible implement, to calculate thermally compensated calibration parameters relating to two-dimensional curvature at the common longitudinal location to optical wavelength shifts of the set of fiber Bragg gratings, wherein the two-dimensional curvature is determined relative to the reference frame associated with the fiducial markers attached to the rigid portion of the shape-sensing elongate flexible implement.

In another aspect, there is provided a calibration apparatus for use calibrating a relationship between wavelength shift and curvature for a shape-sensing elongate flexible implement, the calibration apparatus comprising:

one or more guiding features suitable for receiving the shape-sensing elongate flexible implement and bending the shape-sensing elongate flexible implement along a known curved profile; and fiducial markers for detecting an orientation of the calibration apparatus during calibration of the shape-sensing elongate flexible implement.

In another aspect, there is provided a calibration apparatus for use calibrating a relationship between wavelength shift and curvature for a shape-sensing elongate flexible implement, the calibration apparatus comprising:

a first curved channel configured receive the shape-sensing elongate flexible implement and bend the shape-sensing elongate flexible implement according to a first known curved profile; and a second curved channel configured to receive the shape-sensing elongate flexible implement and bend the shape-sensing elongate flexible implement according to a second known curved profile;

wherein each channel is keyed to a corresponding feature on the shape-sensing elongate flexible implement, such that the shape-sensing elongate flexible implement is inserted into each channel in a common angular orientation relative to a rotational axis of the shape-sensing elongate flexible implement.

In another aspect, there is provided a shape-sensing flexible implement comprising:

an elongate flexible body;

a rigid base supporting said elongate flexible body at a location remote from a distal end of said elongate flexible body;

a plurality of shape sensing optical fibers attached to or housed within said elongate flexible body and extending through said rigid base, each shape sensing optical fiber comprising at least one fiber Bragg grating;

wherein each shape sensing optical fiber traverses a strain relief chamber formed within said rigid base; and wherein each shape sensing optical fiber is mechanically supported by said rigid base on both sides of said strain relief chamber, thereby isolating the portions of said shape sensing optical fibers that are housed within said elongate flexible body from external strain.

In another aspect, there is provided a method of determining a dynamic calibration transformation for determining an orientation of a shape-sensing elongate flexible implement, the shape-sensing elongate flexible implement comprising optically addressable fiber Bragg gratings exhibiting a wavelength shift in response to bending of a flexible portion of the shape-sensing elongate flexible implement, the method comprising:

employing a calibration device to bend at least a segment of the flexible portion of the shape-sensing elongate flexible implement according to known curved profiles, relative to a reference frame associated with fiducial markers attached to a rigid portion of the shape-sensing elongate flexible implement, and measuring initial strain-induced wavelength shifts of the fiber Bragg gratings; and removing the flexible portion of the shape-sensing elongate flexible implement from the calibration device;

employing a tracking system to dynamically determine a tracked orientation of the rigid portion of the shape-sensing elongate flexible implement; and processing the initial strain-induced wavelength shifts and the tracked orientation of the rigid portion of the shape-sensing elongate flexible implement to determine the dynamic calibration transformation relating the orientation of the flexible portion of the shape-sensing elongate flexible implement, within a reference frame of the tracking system, to strain-induced wavelength shifts of the fiber Bragg gratings.

A further understanding of the functional and advantageous aspects of the disclosure can be realized by reference to the following detailed description and drawings.

BRIEF DESCRIPTION OF DRAWINGS

Embodiments will now be described, by way of example only, with reference to the drawings, in which:

FIGS. 18A-B show views of an example calibration device for determining calibration parameters that relate curvature to FBG wavelength shift for a set of FBGs of a shape-sensing flexible probe.

FIGS. 18C-D show examples of a calibration device and flexible implement that are configured to mate in two different angular orientations.

FIGS. 19B-D illustrate a mechanism for locking the flexible implement to the calibration device upon full insertion. The mechanism is depicted at various stages of insertion.

DETAILED DESCRIPTION

Figure 1:
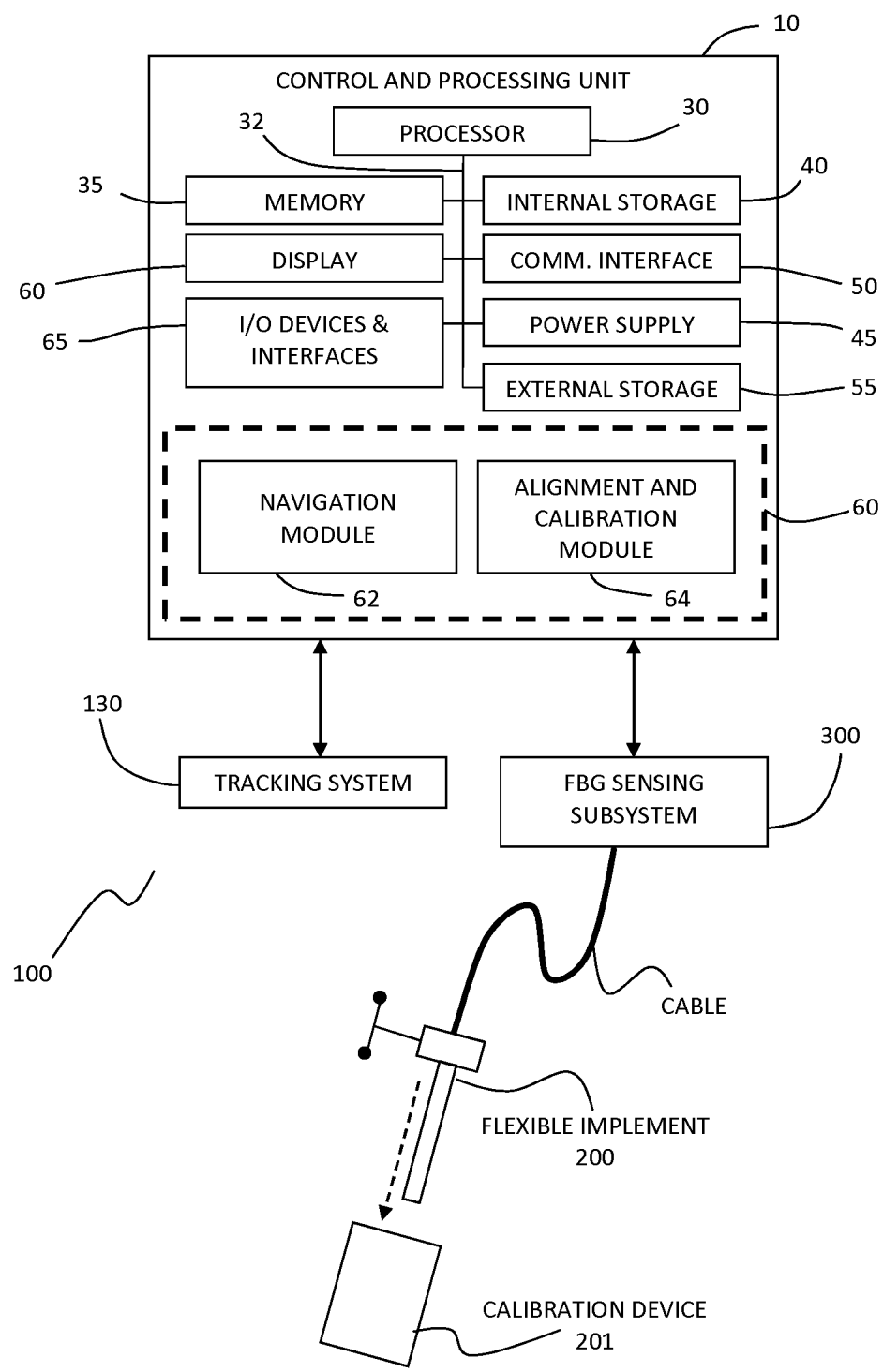
FIG. 1 shows a block diagram of an example system for the intraoperative tracking of a flexible implement.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "flexible implement" generally refers to any type of elongate instrument or tool having a flexible portion. In some example embodiments, a flexible implement may be configured for medical use, such as, for example, for use during surgery, diagnosis or other medical examinations or procedures. In some example embodiments, an elongate flexible implement may have a longitudinal axis that is associated with one or more segments that undergo deflection/bending during normal use. The longitudinal axis may be defined by a longitudinal shaft. Non-limiting examples of flexible implements include catheters, electrodes, endoscopes, needles, K-wires, and microvascular Doppler probes. A flexible implement may be configured to be handheld, or robotically supported and positioned.

As used herein, the term "tracking system" refers to a device or system that allows the detection of the spatial position and orientation of an object in three dimensions (3D). In some example embodiments, an optical tracking system may be configured to operate with visible or infrared light, and may include stereo cameras to detect the positions of passive optical markers (e.g. reflective spheres) and/or active optical markers (e.g. light emitting diodes (LEDs)). Other non-limiting examples of tracking systems include electromagnetic tracking systems and structured light tracking systems.

As used herein, the term "marker" refers to a locating indicator that may be affixed or otherwise connected to an implement, patient, subject, instrument, tool, or other component of a surgical system or surgical field, and which is detectable by a tracking system for use in determining a position or location. A marker may be active or passive, and may be detectable using an optical or electromagnetic detector. An example optical passive marker is a reflective sphere, or portion thereof, and an example active optical marker is an LED. Another example of a marker is a glyph, which may contain sufficient spatial and/or geometrical co-planar features for determining a three-dimensional position and orientation. For example, a glyph marker may include at least three corner features, where the three corner features define a plane.

As used herein, the term "marker plane" refers to the plane shared by one or more markers that is attached to a flexible implement, such that the tracking markers are suitable for determining a three-dimensional position and orientation of the flexible implement by the tracking system when the markers are secured to the flexible implement.

As used herein, the phrase "fiber Bragg grating" or "FBG" refers to a periodic variation in the refractive index within the core of an optical fiber creating a Bragg reflector, which reflects and transmits particular wavelengths of light. The reflected wavelength is known as the Bragg wavelength, which has a well-defined linear relationship with the strain and temperature the grating experiences locally.

As used herein, the phrase "FBG sensing system" refers to a system which directs light via fiber optic cables to one or more fiber Bragg gratings on one or more fibers. The wavelength of light reflected from these FBGs is measured by the FBG sensing system. If a strain or temperature change is applied to the FBG, the wavelength of the reflected light shifts in accordance with well-known FBG theory and this shift is detected by the FBG sensing system. Additionally, the FBG sensing may convert these wavelength shifts into local strain and temperature readings, which may then be used to infer the local radius of curvature of the fibers at the positions of the FBGs. These curvature measurements may then be used to fit a model for the deflection profile of the object undergoing the deflection.

As used herein, the phrase "tracked flexible implement" refers to a composite device consisting of a flexible implement to which optical fibers containing FBGs are attached (permanently or removably, for example, housed within an elongate flexible body of the flexible implement) and a rigid segment to which one or more fiducial markers are attached. This enables the implements spatial position, orientation and deformation to be determined by the tracking system and FBG sensing system respectively.

FIG. 1 is a block diagram illustrating an example embodiment of a system for tracking flexible implements 100. System 100 includes control and processing unit 10, a tracked flexible implement 200, a tracking system 130, a FBG sensing subsystem 300, and optionally, a calibration device 201, as described in detail below. The spatial position and orientation of the tracked flexible implement 200 is monitored by tracking system 130, while the local deflection profile of tracked flexible implement 200 is monitored by FBG sensing system 300.

Tracking system 130 typically uses a passive or active stereo camera system to triangulate the position of makers (highly reflective sphere or light emitting diodes) attached to a rigid frame (marker assembly) integrated (removably or otherwise) into the tracked flexible implement 200.

FBG sensing system 300 emits and receives light through one or more optical waveguides to one or more FBGs distributed along the optical waveguides. These optical waveguides containing FBGs are integrated (removably or otherwise) into the tracked flexible implement 200, such that as the implement undergoes deformation the FBG sensing system detects a wavelength shift or broadening in the reflected spectrum, which can be converted into a local strain measurement at the position of the corresponding FBG.

A plurality of FBGs can be distributed along different longitudinal positions and along various transverse axis of the tracked flexible implement 200 to provide spatially distributed strain measurements. These spatially distributed strain measurements can subsequently be used in conjunction with appropriate boundary conditions to accurately determine the deflection profile of the tracked flexible implement 200 in a local coordinate system determined by the spatial distribution of FBGs.

According to some example embodiments described below, position and orientation data from tracking system 130 and local deflection data from FBG sensing system 300 are processed by control and processing unit 10 according to an alignment and calibration transform, such that the deflection of the flexible portion of flexible implement 200 can be determined within a coordinate system associated with the tracking system 130 (or a coordinate system spatially registered to that of tracking system 130). The alignment and calibration transformation, in some embodiments, may be a rotation matrix, translation matrix or other linear or non-linear transforms. As shown in FIG. 1 and further described in detail below, a calibration device 201 may be employed to determine the calibration parameters. The combined position, orientation and deflection data may be processed and employed, for example, by a navigation module 62 (or a separate navigation system) such that the spatial position of the tracked flexible implement 200 can be displayed relative to a 2D or 3D representation of the anatomy derived from image data. Non-limiting examples of image data 160 include MRI, CT, PET, US, etc. Furthermore, image data may be stored in a variety of different formats, non-limiting examples of which are: DICOM, TIFF, JPEG, STL, PLY, PNG, OBJ, and VTP.

Connections between various modules in FIG. 1 (apart from the optical connection between FBG subsystem and flexible implement 200), which enable communications of signals or data between various systems, may be physical cable (e.g. for delivering an electrical or optical signal) such as single mode fiber, LAN or WAN connections, or may be a wireless connection, for example, as an optical transmission modality, or wireless transmission modality such as Wifi, NFC or Zigbee®.

FIG. 1 provides an example implementation of control and processing unit 10, which includes one or more processors 30 (for example, a CPU/microprocessor or a graphical processing unit, or a combination of a central processing unit or graphical processing unit), bus 32, memory 35, which may include random access memory (RAM) and/or read only memory (ROM), one or more internal storage devices 40 (e.g. a hard disk drive, compact disk drive or internal flash memory), a power supply 45, one more communications interfaces 50, external storage 55, a display 60 and various input/output devices and/or interfaces 55 (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, and/or a microphone for capturing speech commands).

Control and processing unit 10 may be programmed with programs, subroutines, applications or modules 60, which include executable instructions, which when executed by the processor, causes the system to perform one or more methods described in the disclosure. Such instructions may be stored, for example, in memory 35 and/or internal storage 40. In particular, in the example embodiment shown, navigation module 62 includes executable instructions for rendering a navigation user interface on a display, in which preoperative image data is spatially registered to the intraoperative reference frame and shown overlaid with a rendering of flexible implement 200 (and is optionally shown with intraoperative image data). Alignment and calibration module 64 includes executable instructions for processing the FBG wavelength shifts measured by FBG sensing subsystem 300, tracked position and orientation data from tracking system 130, in order to determine, based on calibration parameters (e.g. an alignment and calibration transformation), the orientation of the flexible portion of flexible implement 200. Alignment and calibration module 64 may also include executable instructions for guiding and/or automating one or more of the calibration methods that are described herein.

Although only one of each component is illustrated in FIG. 1, any number of each component can be included in the control and processing unit 10. For example, a computer typically contains a number of different data storage media. Furthermore, although bus 32 is depicted as a single connection between all of the components, it will be appreciated that the bus 32 may represent one or more circuits, devices or communication channels which link two or more of the components. For example, in personal computers, bus 32 often includes or is a motherboard. Control and processing unit 10 may include many more or less components than those shown.

In one embodiment, control and processing unit 10 may be, or include, a general purpose computer or any other hardware equivalents. Control and processing unit 10 may also be implemented as one or more physical devices that are coupled to processor 130 through one of more communications channels or interfaces. For example, control and processing unit 10 can be implemented using application specific integrated circuits (ASICs). Alternatively, control and processing unit 10 can be implemented as a combination of hardware and software, where the software is loaded into the processor from the memory or over a network connection.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refers to all computer-readable media, except for a transitory propagating signal per se.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

Figure 2A:
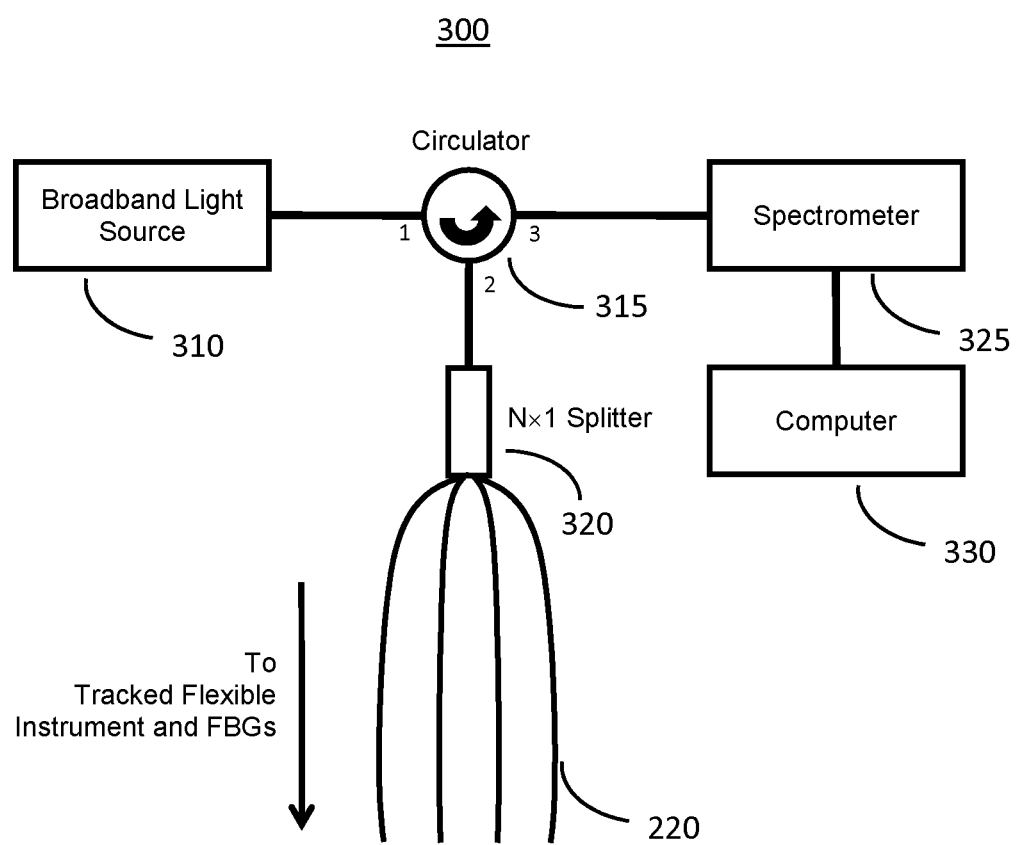
FIG. 2A shows an example of an optical subsystem for measuring optical signals associated with strain that is applied to fiber Bragg gratings (FBGs).
Figure 2B:
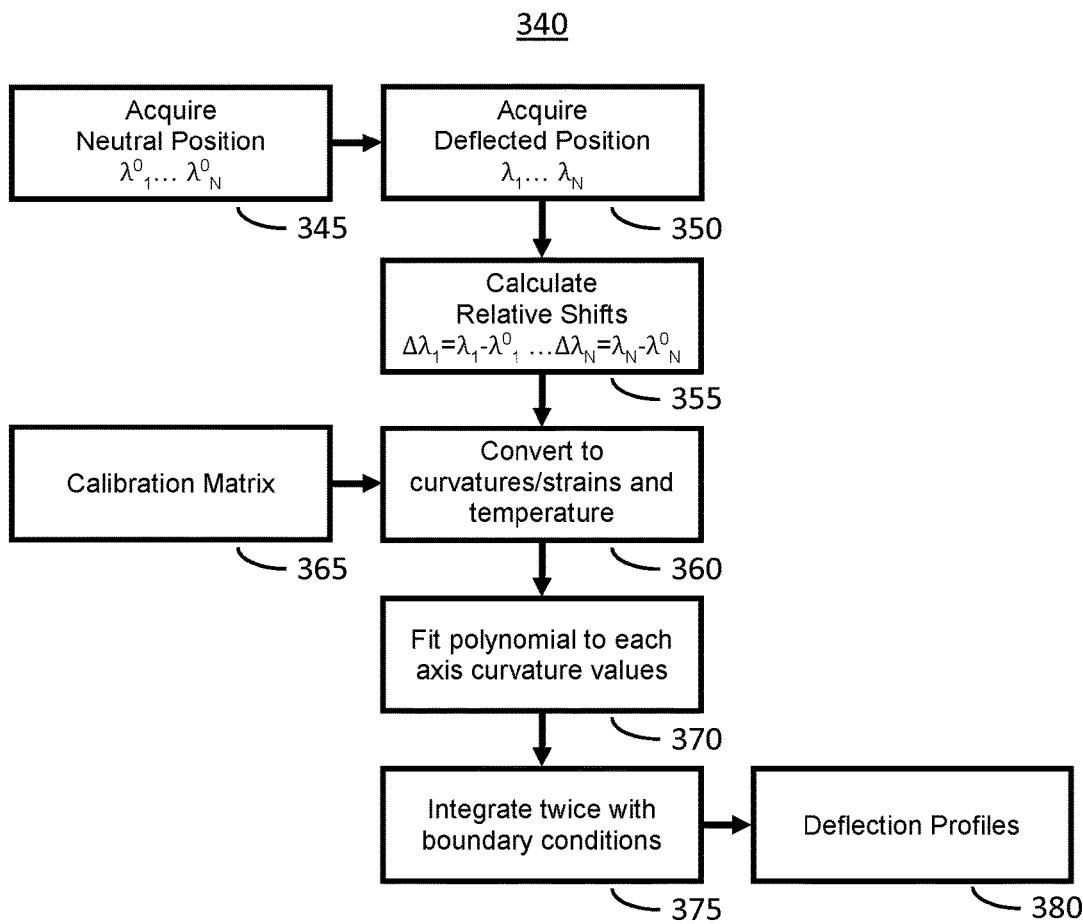
FIG. 2B shows an example method for measuring optical signals associated with strain that is applied to fiber Bragg gratings (FBGs), and employing calibration parameters to determine to curvature (and deflection profile) of a flexible implement housing the FBGs.

FIGS. 2A and 2B shows a schematic of an example FBG sensing system 300 and associated flow chart, respectively. The system and methods shown are presented here simply to facilitate understanding and for completeness.

In FIG. 2A, example FBG sensing system 300 includes broadband light source 310, optical circulator 315, N×1 splitter 320, Noptical waveguides/fibers 220, spectrometer 325 and computer 330. Optical fibers/waveguides 220 each include one or more FBGs, or are each in optical communication with respective optical fibers/waveguides or waveguides having FBGs formed therein. Broadband light source 310 emits light with an optical spectrum suitable for interrogating the FBGs. Emitted light enters port 1 of optical circulator 315, exits out of port 2 into N×1 splitter 320 and is split into optical fibers/waveguides 220 where it then travels down to the tracked flexible implement to interact with the FBGs. The Bragg wavelength of each FBG is reflected back through optical fibers/waveguides 220 into N×1 splitter 320, where all reflected signals recombine, and enters port 2 of optical circulator 315. Light entering port 2 of optical circulator 315 is directed out of port 3 and to spectrometer 325, where the reflected spectrum is captured and processed by computer 330 (it will be understood that computer 330 may be a subcomponent of control and processing unit 10 shown in FIG. 1). It will be understood that the system shown in FIG. 2A is but one example system, and that other system configurations may alternatively by used. For example, in an alternative embodiment, broadband light source 310 and spectrometer 325 can be replaced with a tunable laser and single element detector. The readout of reflected Bragg wavelengths may be recorded as a function of time and processed by computing device 300 in order to compute the time-dependent orientation of the tracked flexible instrument.

FIG. 2B shows a flow chart 340 for conversion of wavelengths to strain and deflection profiles, which may be stored on computer 330 or on another processing device. Flow chart 340 analyzes data sent from spectrometer 325 and converts this data to deflection profiles of tracked flexible implement 200. First, Bragg wavelengths in each of the NFBGs are measured with the flexible implement 200 being in neutral position $\lambda^o_i$ in step 345 and deflected $\lambda_i$ in step 350 in order to calculate the corresponding wavelength shifts $\Delta\lambda_i = \lambda_i - \lambda^o_i$ in step 355. These shifts are then converted to curvature values in step 360 either through an empirically or theoretically derived calibration matrix 365. In practice, empirically measured calibration matrixes are used due to possible manufacturing errors such a misalignment of FBGs [1].

In the case of a cantilever beam type device, the curvature values for each axis at multiple (N) longitudinal FBG locations can then be fit using an $N^{th}$ order polynomial function in step 370. By integrating this polynomial function twice with appropriate boundary conditions in step 375, an $(N+2)^{th}$ order polynomial for the deflection profile 380 in each axis is obtained [1]. It is noted that while Bragg peak wavelength shifts are described here to measure curvatures and strains, it is also possible to measure the broadening of the Bragg peaks in order to determine these quantities [2].

Figure 3:
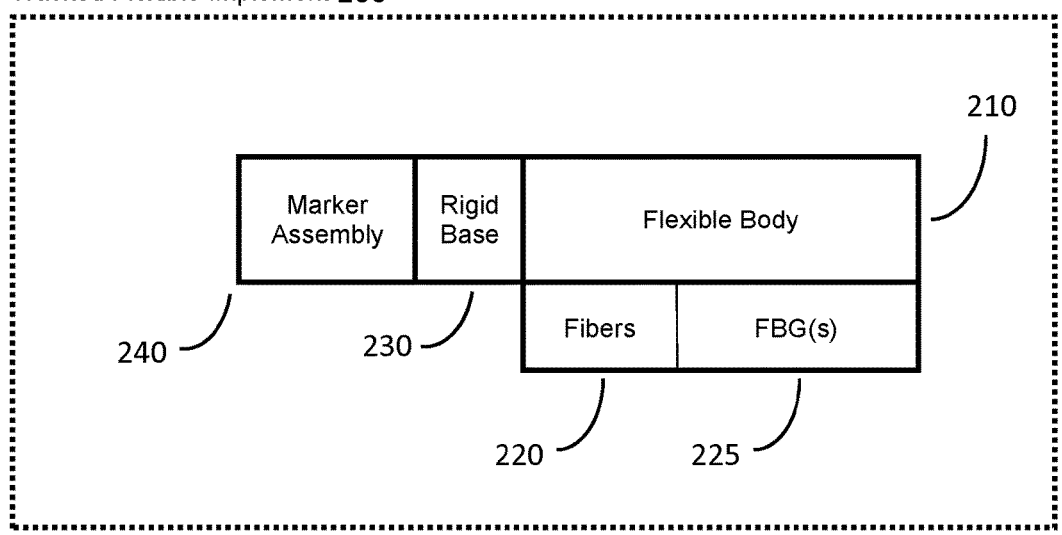
FIG. 3 shows a block diagram illustrating components of an example tracked flexible instrument.

FIG. 3 shows a schematic representation of an example tracked flexible implement 200. It comprises a flexible body portion 210, one or more optical fibers 220, one or more FBGs 225 within one or more optical waveguides (cores) within the optical fibers, a rigid base 230 and marker assembly 240. Tracked flexible implement 200 may be one of any number of commonly used devices such as catheters, needles, wires, endoscopes, probes etc. Fibers 220 and FBGs 225 are distributed at various spatial locations inside or around the flexible body portion 210, such that, if the flexible body portion 210 undergoes a deflection, the FBGs also undergo the same deflection. Various FBG configurations will be discussed subsequently. The deflection of flexible body portion 210 of tracked flexible implement 200 are made relative to rigid base 230—one example of such a rigid base is a needle hub. Rigid base 230 also provides a location, where marker assembly 240 may be attached (removably or otherwise), fixing the position and orientation of marker assembly 240 relative to rigid base 230.

In some embodiments, rigid base 230 is incorporated into marker assembly 240. For example, when tracking the deformation of a flexible device containing the FBGs, marker assembly 240 may be clamped onto the device at a location and orientation relative to the FBGs. This clamping location creates a rigid base 230 relative to which deflections may be measured.

As described in further detail below, tracked flexible implement 200 may also include one or more keyed features, such that the tracked flexible implement 200 can be inserted into a calibration device (having associated mating keyed features) in a known orientation.

Figure 4:
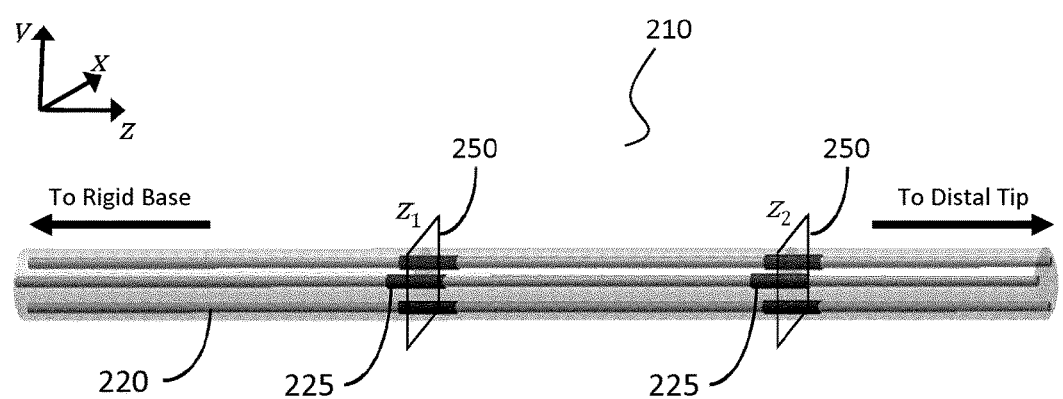
FIG. 4 shows an internal view of the flexible portion of an example flexible implement, showing the internal fibers and sets of FBGs for shape sensing.

FIG. 4 shows a drawing of a flexible portion 210 of an example tracked flexible implement 200. In this drawing, three optical fibers 220 with three FBGs 225 at two longitudinal (z-axis) locations ($z_1$ and $z_2$) are shown. It is advantageous to position at least three FBGs 225 with different Bragg wavelengths at each longitudinal position (z-axis) in a transverse planes 250, since the strains measured in each of the aligned FBGs 225 are then linear combinations of the strains in direction of the main axes (i.e. x and y) of the transverse plane 250. Using at least three FBGs at the same longitudinal (z-axis) location allows therefore to decouple the x- and y-axis strains as well as temperature in step 350. Multiple transverse FBG configurations and fixation methods, which are advantageous for the accurate measurement of strain and deflection profiles, are presented below.

Figure 5A:
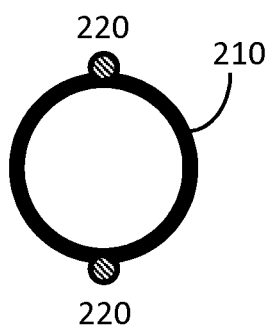
FIGS. 5A-C show cross-sections of the flexible portion of various example flexible implements in which the optical fibers are attached thereto.
Figure 5B:
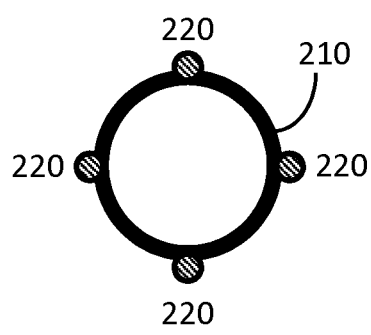
Figure 5C:
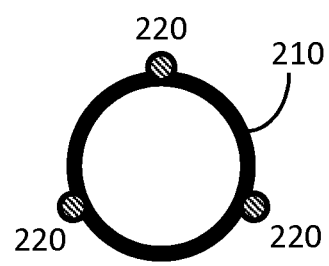

FIGS. 5A-C show a number of example transverse cross-sectional schematics 250 depicting various fibers 220 or FBGs 225 orientations and techniques for securing the fibers 220 and FBGs 225 to flexible body portion 210. While only one single transverse plane 250 is shown depicting orientation and position of fibers 220 and FBGs 225, it is understood that a plurality of FBGs may be distributed longitudinally (z-direction) along the plurality of fibers either before or after the plane shown, in order to measure strains at multiple longitudinal positions (z) along flexible implement 200. In some embodiments fibers/FBGs 220/225 may be attached to, or housed within, flexible body portion 210 through the use of adhesives such as epoxies or tapes. In some embodiments, flexible body portion 210 may also have grooves to accept fibers/FBGs which facilitate accurate positioning.

In FIG. 5A, the fibers/FBGs 220/225 are attached externally to flexible body portion 210. In this example embodiment, bending is measured relative to a single axis using a two fiber symmetric design, which can be used to effectively recover strains and remove temperature effects through direct subtraction of the two FBG readings. FIG. 5G shows an example symmetric four fiber configuration with fiber/FBG 220/225 secured externally to flexible body portion 210. Four fiber configurations facilitate simple removal of temperature effects through direct subtraction of symmetric pairs of FBGs readings. FIG. 5C shows fibers/FBGs 220/225 attached externally to flexible body portion 210. The angular separation between fibers/FBGs is 120°, allowing for temperature compensation and x- and y-axis strains to be obtained. Each of the three previous examples used direct external fixation to the flexible body portion 210, however direct internal fixation of the fibers, or embedded fibers, to flexible body portion 210, is also possible.

Figure 6A:
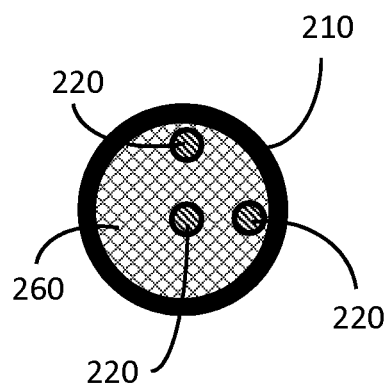
FIGS. 6A-D show cross-sections of the flexible portion of various example flexible implements in which the optical fibers are supported within a multi-lumen structure.

FIG. 6A shows an example internal three fiber design. In this example embodiment, attachment of fiber/FBGs 220/225 is mediated through the use of a multi-lumen insert 260. Fibers/FBGs 220/225 are inserted into multi-lumen insert 260 with an adhesive compound to secure fibers/FBGs 220/225 to multi-lumen insert 260. Multi-lumen insert 260 may then be inserted securely into flexible body portion 210 (removably or otherwise). The fiber/FBGs 220/225 in FIG. 6A utilize a central fiber to isolate only temperature effects in situations, where central fiber/FBG 220/225 lies along the neutral axis of flexible body portion 210. The remaining two fiber/FBGs are in an orthogonal configuration to measure strains along those axis independently of one another.

Figure 6B:
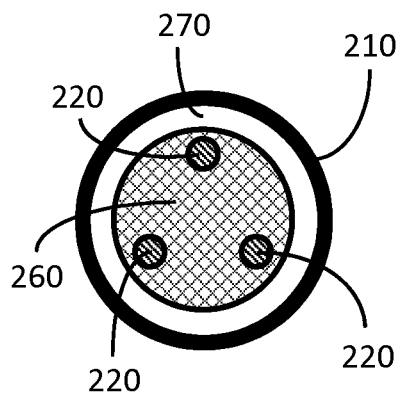

FIG. 6B shows an example embodiment of an internal multi-lumen catheter 260 design with three fibers/FBGs 220/225 in a symmetric 120° arrangement with an inflatable balloon 270. After insertion of multi-lumen insert 260 into flexible body portion 210, inflatable balloon 270 is expanded to secure multi-lumen insert 260 to flexible body portion 210 (friction fit).

Figure 6C:
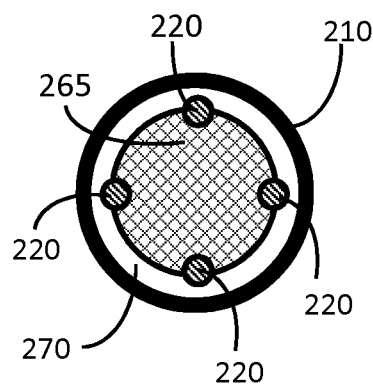
Figure 6D:
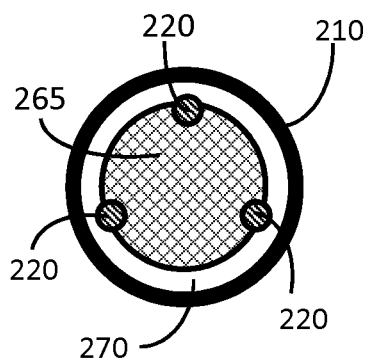

FIG. 6C shows an example embodiment of a four fiber/FBG 220/225 notched insert 265 design with inflatable balloon 270. Notches in insert 265 are used as alignment and securing aid (using adhesives or otherwise) for fibers/FBGs 220/225, but in some may be omitted and direct surface fixation to insert 265 may be used. FIG. 6D shows an embodiment of a three fiber/FBG 220/225 notched insert design 265 with inflatable balloon 270.

Figure 7A:
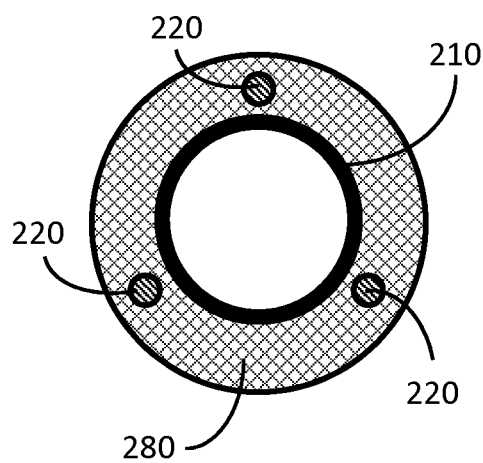
FIG. 7A-D show cross-sections of the flexible portion of various other example flexible implements in which the optical fibers are supported within a multi-lumen structure.
Figure 7B:
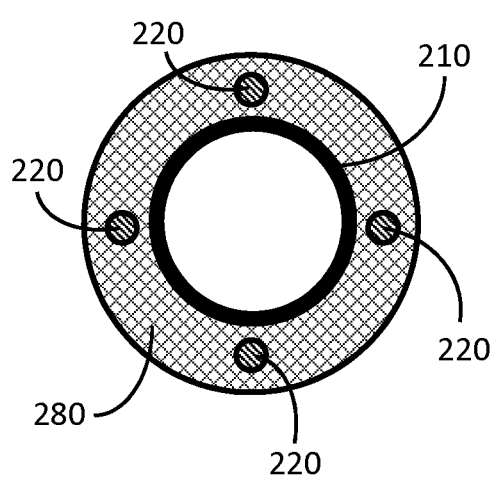
Figure 7C:
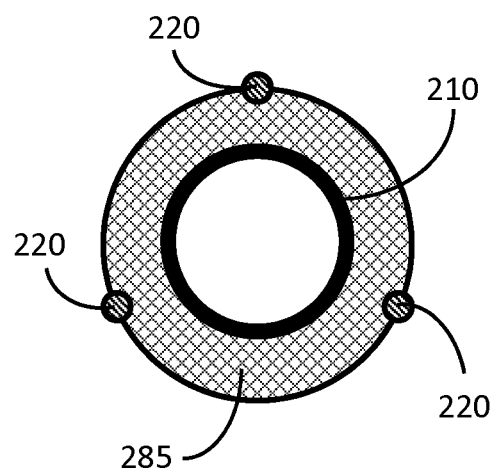
Figure 7D:
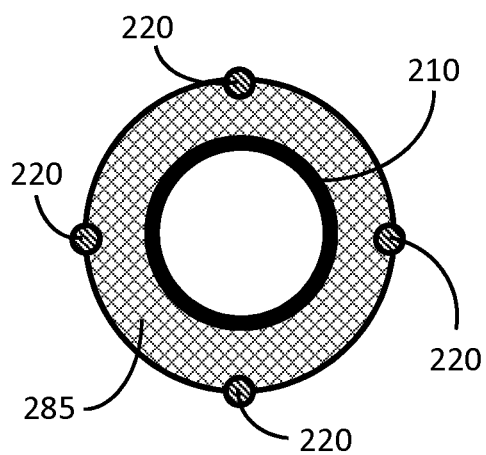

FIG. 7A shows an example embodiment of a symmetric (120°) three fiber/FBG 220/225 external sheath 280 design with three lumens holding fibers/FBGs 220/225. Flexible body portion 210 is inserted into external sheath 280 and secured via friction fit or otherwise. FIG. 7B shows an example embodiment of a symmetric four fiber/FBG 220/225 external sheath 250 design with four lumen holding fibers/FBGs 220/225. FIG. 7C shows an example embodiment of a symmetric three fiber/FBG 220/225 notched external sheath 285 design and FIG. 7D shows an example embodiment of a symmetric four fiber/FBG 220/225 notched external sheath 285 design.

Figure 8A:
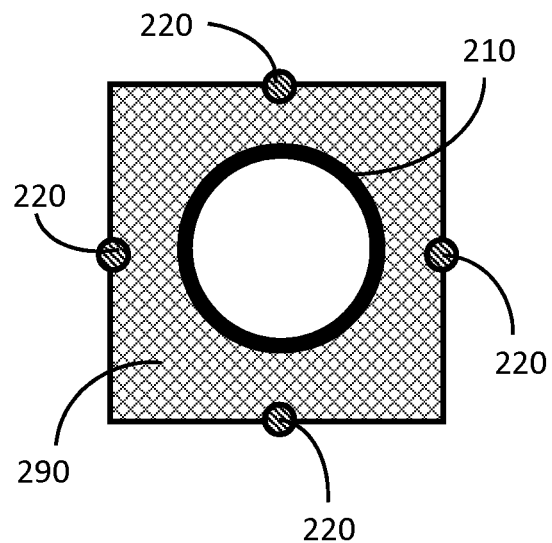
FIGS. 8A-B show two examples of different cross-sectional shapes of the flexible portion of the flexible implement.
Figure 8B:
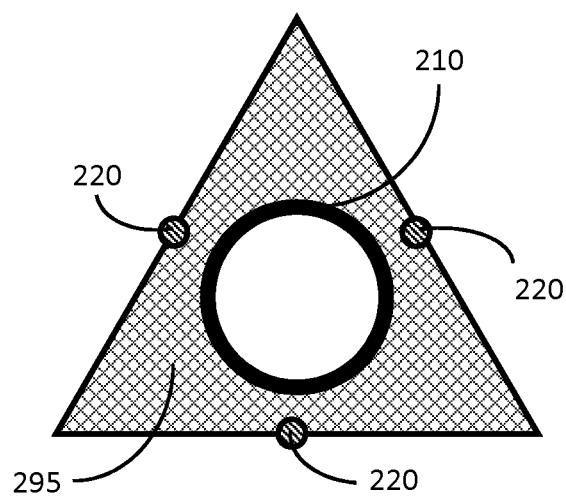

FIG. 8A shows an example embodiment of a symmetric square sheath 290 design with four fiber/FBG 220/225 notched externally. The square sheath 290 can help improve manufacturability (positioning and attachment of fibers/FBGs 220/225) over previously shown circular designs. FIG. 8B shows an example three fiber/FBG 220/225 externally notched triangular sheath 295 design.

In FIGS. 4 to 8A-B, the fibers can be physically secured to the sheath or catheter type structures using a number of methods. Non-limiting example methods include use of UV, heat or air cured epoxies, glues, silicones or similar adhesives to pot the fibers within the channels. In some example assembly procedures, these liquids can be forced through the channels after which the fibers are fed through. This method secures the fibers at all points within the flexible body and allows for reliable strain readings. For external sheath configurations, the fiber should be secured at least at locations where the FBGs lie to the sheath surface securely to enable accurate measurements of strain. However, in practice it is beneficial to secure as much fiber as possible to the sheath surface. Securing fibers to the external portion of a sheath could be performed by first tacking the fibers to the surface with one of the adhesives or similar product mentioned above. Once the FBGs are tacked securely in place, the distal and proximal ends of the sheath can be plugged to prevent ingress of adhesive and a portion of or all of the sheath may be dipped into the adhesive to secure and protect the fibers. Once dipped, the excess adhesive can be removed via gravity drainage or similar methods after which the adhesive can be cured. Once cured the plugs used to prevent adhesive ingress can be removed.

Although the example embodiments illustrated in FIGS. 4-8B involve separate fibers, it will be understood that in alternative embodiments, a multi-core fiber may be employed, where a single optical fiber is formed with multiple cores, and where the shape-sensing FBGs are formed within each core.

Figures 9A, 9B:
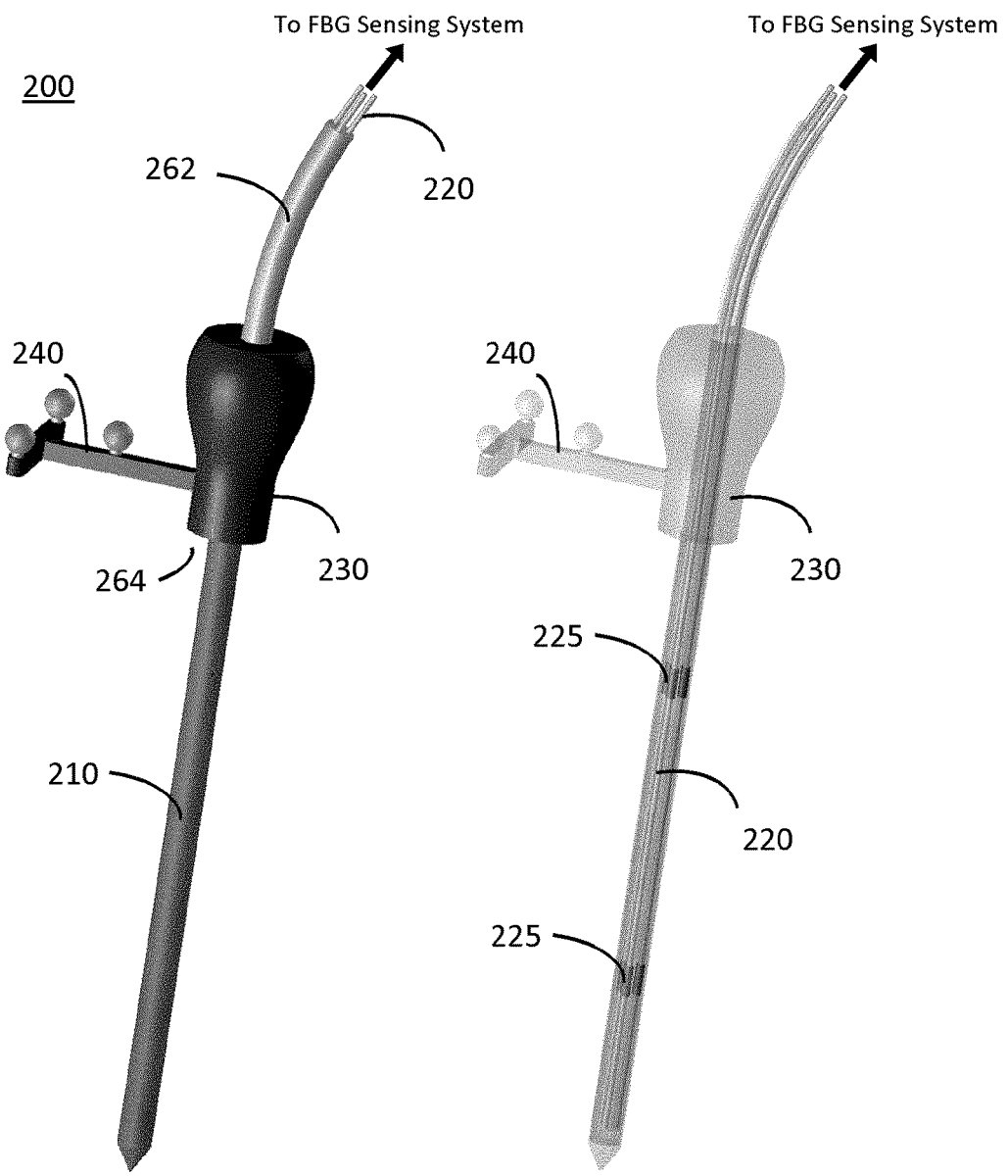
FIGS. 9A-B show (A) solid and (B) transparent view of an example flexible implement having an elongate flexible portion and a rigid base, and where fiducial markers are supported by the rigid base.

FIG. 9A shows a drawing of an example of a tracked flexible implement 200, with a marker assembly 240 for optical tracking of the spatial location and orientation of the flexible implement 200, and a rigid base 230, which is in this case the handle of the flexible implement. For the deflection measurement, at least three optical fibers 220 with respective FBGs 225 are positioned at one or more longitudinal positions (the present example implementation shows two longitudinal positions) inside the flexible body portion 210, as can be seen in the semi-transparent view in FIG. 9B.

In some embodiments, a cabling (for example, cable 262 with embedded fibers 220 in FIGS. 8A-B) connects tracked flexible implement 200 to FBG sensing system 300 and/or other system components. This cabling, extends from rigid base 230 in a proximal direction, may transfer unwanted strains to FBGs 225 located within flexible body 210 and therefore compromise the deflection measurement. Alternatively, rigid base 230 may include a connection device for connecting the optical fibers that are attached to, or housed, within flexible body 210, to an external optical cable. The connection device may be, for example, a parallel connector device, such as an MPO or MTP multifiber connector, or a connector for connecting two multi-core fibers.

In order to isolate proximal strains from FBGs 225, rigid base may incorporate, house, or otherwise support or contain a strain isolation mechanism for reducing or substantially eliminating the effect of external longitudinal strain on the deflection measurement.

Figure 10A:
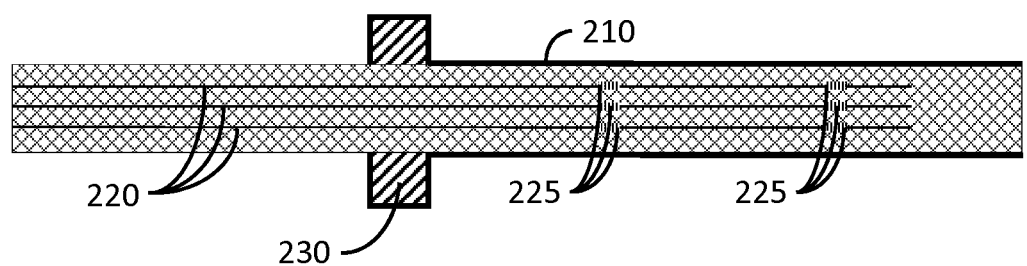
FIG. 10A shows a cross-sectional view of an example flexible implement, showing the incorporation of a rigid base.

FIG. 10A shows a longitudinal cross section of the example flexible implement in FIGS. 9A-B. Three optical fibers 220 and two sets of three FBGs 225 are held inside flexible body 210. Flexible body 210 with embedded fibers 220 extend through rigid base 230, where movement of flexible body 210 on a proximal side of rigid base 230 (opposite to the distal side housing the FBGs) can induce strain effects on the FBGs.

Figure 10B:
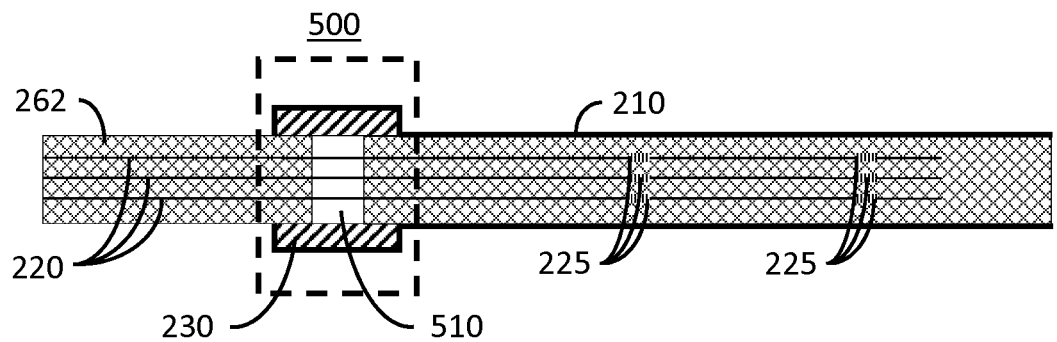
FIG. 10B shows a cross-sectional view of another example flexible implement, showing the incorporation of a rigid base that functions as a strain relief mechanism.

FIG. 10B illustrates an example strain isolation mechanism 500, which includes a rigid base 230 having an internal longitudinal chamber 510 (i.e. an internal longitudinal gap) formed therein. Fibers 220 are attached to or housed within flexible body 210, which extends in a distal direction from rigid base 230. (As shown in the figure, flexible body 210, which houses fibers 220, is attached to one side of rigid base 230 (the distal side), and a proximal cable 262, also housing fibers 220, is attached to the other side of rigid base 230 (the proximal side), such that fibers 220 are mechanically supported on either side of longitudinal chamber 510, and such that fibers 220 traverse longitudinal chamber 510.

This example mechanism, and variations thereof, reduces the propagation of strain from the proximal cable 262 to fibers within flexible body 210210. In some embodiments proximal cable 262 may be formed from the same material, and/or may have the same geometry, as flexible body 210, while in other example implementations, proximal cable and flexible body 210 may be have a different geometry and/or structure (e.g. material composition). In other embodiments proximal cable 262 may be replaced with a plurality of smaller cables or tubes, each housing one or more fibers.

In the example embodiment illustrated in FIG. 10B, rigid base 230 may have one or more markers directly or indirectly attached thereto. In other example embodiments, rigid base 230 (having longitudinal chamber 510 formed therein) may be connected or otherwise attached to one or more rigid components. For example, an additional rigid component may be provided as a handle or rigid structure for attachment of markers thereto. In one example embodiment, an inner rigid sheath may be housed within an outer rigid base.

Figure 11:
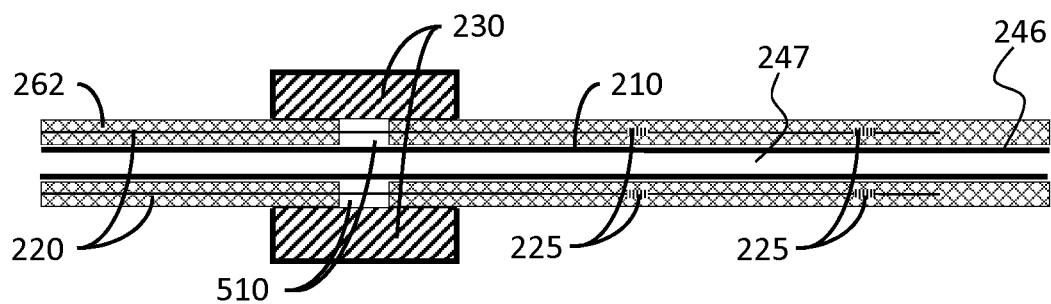
FIG. 11 shows a cross-sectional view of another example flexible implement, showing the incorporation of a rigid base that functions as a strain relief mechanism, where an internal conduit traverses an internal chamber of the strain relief mechanism.

With reference to FIG. 11, another example strain isolation mechanism is shown in which flexible body 210 includes a (see FIGS. 7A-D and 8A-B) with two optical fibers 220 and two sets of three FBGs 225 housed within flexible body 210. As in FIG. 10B, rigid base 230 has longitudinal chamber 510 formed therein, and flexible body 210, which houses fibers 220, is attached to one side of rigid base 230 (the distal side), and a proximal cable 262, also housing fibers 220, is attached to the other side of rigid base 230 (the proximal side), such that fibers 220 are mechanically supported on either side of longitudinal chamber 510, and such that fibers 220 traverse longitudinal chamber 510. However, in the present example embodiment, an inner conduit 246 extends through proximal cable 262, rigid base 230, and flexible body 210. As shown in the figure, inner conduit 248 traverses internal longitudinal chamber 510 such that the inner lumen 247 of inner conduit 248 is not in fluid communication with internal longitudinal chamber 510. In other example implementations, components such as, but not limited to, optical fibers, electrical signal cables and a torque cable may extend through internal channel 510, in addition to, or in alternative to, internal conduit 246.

Figure 12A:
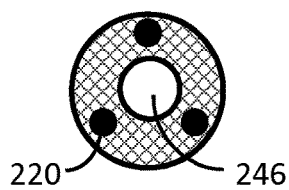
FIGS. 12A-E show cross-sections of the flexible portion of various example flexible implements in which an internal conduit is provided.
Figure 12B:
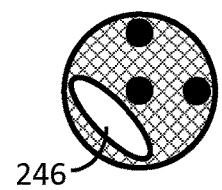
Figure 12C:
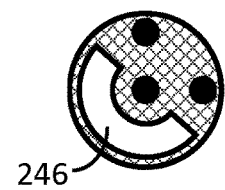
Figure 12D:
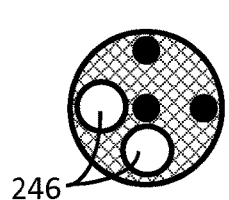
Figure 12E:
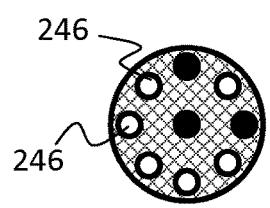

FIGS. 12A-E show a number of illustrations of example transverse cross-sections of flexible body 210, according to various non-limiting example embodiments. Flexible body 210, supports various fibers 220 having FBGs and incorporates one or more internal channels 246 that allow distal access. In some example embodiments, internal channel(s) 246 could be used for delivery of liquids (water, drugs, etc.), gas, or/and holding other optical fibers, instruments or/and electric cables. FIG. 12A shows an example embodiment of flexible body 210 with three fibers 220 in a symmetric 120° arrangement and one internal channel 246 in the center. In FIG. 12B to FIG. 12E, three fibers 220 are arranged in an orthogonal configuration with a central fiber on the neutral axis to isolate only temperature effects. The example embodiments shown FIG. 12B and FIG. 12C each have an internal channel 246, but with different respective shapes. The example embodiment shown in FIG. 12D has two internal channels 246. FIG. 12E shows an example embodiment with six internal channels 246.

Figure 13A:
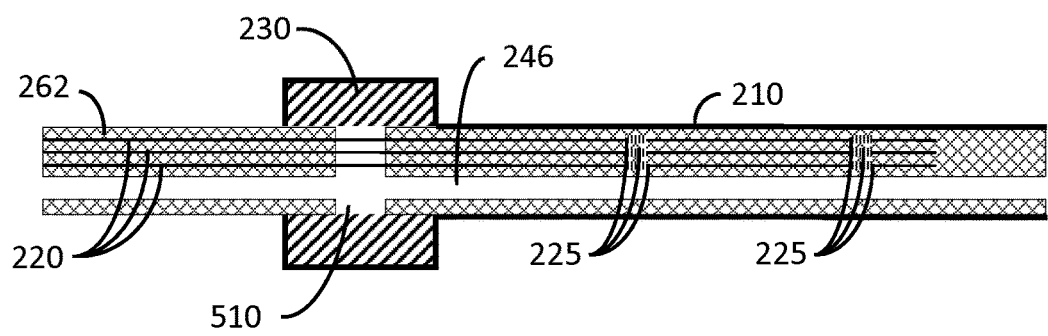
FIGS. 13A-B show a cross-sectional views of another example flexible implements, showing the incorporation of a rigid base that functions as a strain relief mechanism, where an internal channel in provided in the flexible portion of the flexible implement, and in a proximal cable interfaced with the rigid base.
Figure 13B:
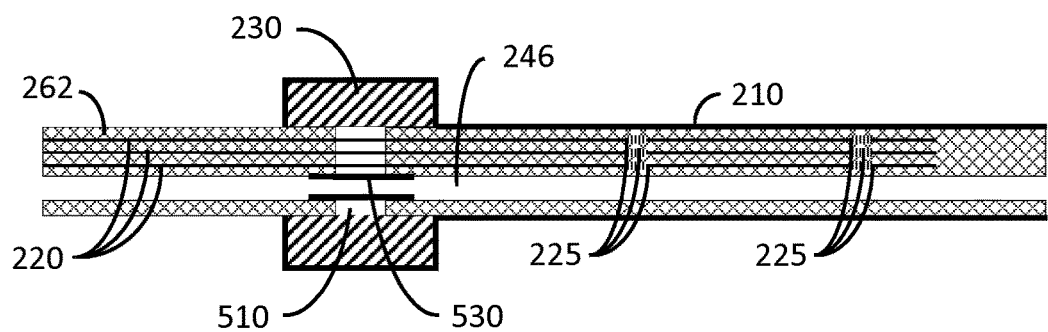

FIGS. 13A and B show longitudinal cross sections associated with two embodiments involving an internal channel 246. As in the preceding example embodiments, rigid base 230 includes an internal longitudinal chamber 510 for strain isolation. In FIG. 13A, flexible body 210 and proximal cable 262 includes internal channel 246, the inner lumen of which is in fluid communication with internal longitudinal chamber 510 within rigid base 230. FIG. 13B shows an another example embodiment, in which a bridging conduit 530 (e.g. light wall tubing) is employed to direct contents of distal access channel 246 across internal longitudinal chamber 510 without bringing the inner lumen of internal channel 246 into fluid communication with internal longitudinal chamber 510.

In general, FBGs will measure the wavelength shifts in a non-orthogonal coordinate system, which is defined by the positions of the FBGs relative to the neutral axis and oriented to any other coordinate system such as that defined by the marker plane attached to the tool.

In some example embodiments, calibration methods and devices are provided that enable the use internal FBGs to determine the local curvature of a tracked flexible shape sensing device within known coordinate system. While a full two dimensional formulation is described here, the same method also applies to the one dimensional case, where only bending in a single axis is needed.

In the following example, two FBGs are provided within a flexible shape sensing device at longitudinal position z, and are oriented along arbitrary transverse axis (p, q). In order to determine the local curvature of the flexible shape sensing device, the curvatures should be measured in a known orthogonal coordinate system (x, y). Applying known strains in two independent directions yields (i=1,2) a pair of normalized measurements $(p_1, q_1)$ and $(p_2, q_2)$ respectively, where the normalization is given by, $$p_i(z) = \frac{\lambda_1^i - \lambda_1^0}{\lambda_1^0} \quad (4)$$

$$q_i(z) = \frac{\lambda_2^i - \lambda_2^0}{\lambda_2^0} \quad (5)$$

where $\lambda_1^i$ and $\lambda_2^i$ are the Bragg wavelengths measured during i-th applied strain direction in the first FBG and the second FBG respectively. $\lambda_1^0$ and $\lambda_2^0$ are the Bragg wavelengths measured in the two FBGs with the flexible implement being in a reference configuration which would usually be the neutral position (a position in which the FBG's experience minimal strain) but could more generally be a known profile in which the FBG's experience a measurable strain.

In the present example embodiment, the two known strains are applied in the x and y directions relative to the neutral reference configuration, so that the resulting curvatures $\rho_x$ and $\rho_y$ are related to the normalized measurement by:

$$\begin{bmatrix} \rho_x \\ 0 \end{bmatrix} = \begin{bmatrix} a & b \\ c & d \end{bmatrix} \begin{bmatrix} p_1 \\ q_1 \end{bmatrix} \quad (6)$$

$$\begin{bmatrix} 0 \\ \rho_y \end{bmatrix} = \begin{bmatrix} a & b \\ c & d \end{bmatrix} \begin{bmatrix} p_2 \\ q_2 \end{bmatrix} \quad (7)$$

where $$\begin{bmatrix} a & b \\ c & d \end{bmatrix}$$

is the calibration matrix (the generalization for the known reference configuration would involve the addition of known constants to the strains (inverse of curvature)), which can be determined through the following equation:

$$\begin{bmatrix} a & b \\ c & d \end{bmatrix} = \frac{1}{DET(R)} \begin{bmatrix} \rho_x & 0 \\ 0 & \rho_y \end{bmatrix} \begin{bmatrix} q_2 & -q_1 \\ -p_2 & p_1 \end{bmatrix} \quad (8)$$

where R is defined as, $$R = \begin{bmatrix} p_1 & p_2 \\ q_1 & q_2 \end{bmatrix}. \quad (9)$$

More generally, the Moore Penrose pseudoinverse, or another suitable method for solving an overdetermined system, may be used for determining the calibration matrix if more than two measurements are made.

In order to determine curvature based on the strain applied to an FBG, as it is assumed for equations (6) and (7), the location of the FBG along the longitudinal axis of the instrument has to be known. However, it may be the case that the precise longitudinal location of a FBG may be unknown—for example due to production tolerances. In the following discussion, example methods are provided for determining the longitudinal position of a FBG.

According to one example embodiment, the flexible implement may be bent along two deflection profiles, $D_1(z)$ and $D_2(z)$, with different orders in z. Two example deflection provides are:

$$D_1(z) = A_1 z^4, \quad (10)$$

$$D_2(z) = A_2 z^3, \quad (11)$$

where $A_1$ and $A_2$ are scaling coefficients controlling the amount of deflection (e.g. lateral displacement at the distal end of the flexible implement).

Accordingly, the ratio of the curvature profiles for the two deflection profiles is given by:

$$\frac{\rho_1}{\rho_2} = \frac{d^2 D_1(z)/dz^2}{d^2 D_2(z)/dz^2} = 2 \frac{A_1}{A_2} z \quad (12)$$

Since the ratio of the curvatures is equal to the ratio of the corresponding wavelength shifts $\Delta\lambda_1$ and $\Delta\lambda_2$ measured in a FBG, its longitudinal position $z_{FBG}$ can be determined using:

$$z_{FBG} = \frac{A_2}{2A_1} \frac{\Delta\lambda_1}{\Delta\lambda_2} \quad (13)$$

Figure 14A:
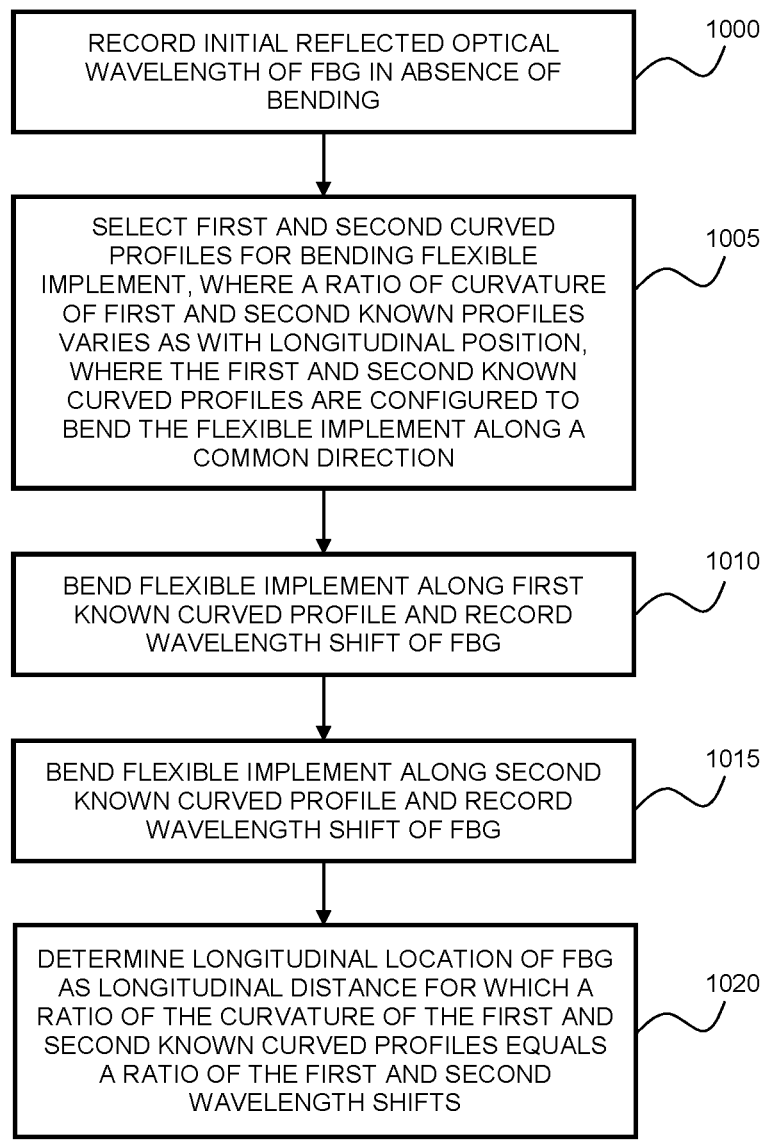
FIG. 14A is a flow chart describing an example method of calibrating the longitudinal location of a FBG within a flexible implement.

Referring now to FIG. 14A, a flow chart is shown that illustrates an example method of calibrating the longitudinal location of a fiber Bragg grating within a flexible implement. In step 1000, optical measurements are made to determine the reflected wavelength (e.g. the wavelength of the reflected peak) of a FBG residing within a flexible implement, where the measurements are made in the absence of bending. First and second known curved profiles are then determined or provided, such that the ratio of curvature of the first and second known profiles varies with longitudinal position. In other words, the curvature of the first known curved profile and the second known profile, as determined as a function of longitudinal distance along each curved profile, are provided such that the ratio of the curvatures varies with longitudinal distance. The first and second known profiles are also selected such that the first and second known curved profiles are bend the flexible implement along a common direction (i.e. within a common plane, or within parallel planes) as shown at 1005. Here, the phrase "known" refers to a curved profile having a known mathematical shape (e.g., as described by a function, set of discrete points, or other mathematical form).

The flexible implement is then bent according to the first and second known curved profiles, and the associated wavelength shifts are measured, as shown at 1010 and 1015. The longitudinal position of the FBG is then determined according to the method described above. As shown at 1020, the longitudinal position of the FBG is given by the longitudinal position at which the ratio of the curvatures of the first and second known curved profiles equals the ratio of the first and second measured wavelength shift. The preceding method may be repeated for one or more additional FBGs that reside within the flexible implement.

The first and second known curved profiles may be selected such that the ratio of their curvatures is single valued within longitudinal region of interest where one or more FBGs are expected to reside. In some embodiments, if the flexible implement is known to have a Bragg grating located within a given range of longitudinal positions, the first and second known curved profiles may be selected such that the ratio of the curvatures varies with longitudinal distance, and is single valued, within the given range of longitudinal positions.

The first and second known curved profiles may take on many different forms, provided that the ratio of their curvature is zero and is single-valued over at least a portion of their lengths. In one example implementation, the curved profiles are polynomials of different degrees, wherein each degree is at least two, as shown in the preceding example.

In some example embodiments, the two deflection profiles may be provided by a calibration device that includes guiding features that are suitable for receiving the flexible implement and bending the flexible implement according to the first and second known curved profiles. The guiding features are provided such the ratio of the curvature of the first and second known curved profiles varies with longitudinal distance, and such that the first and second known curved profiles bend the flexible implement along a common direction, as noted above. The aforementioned method may be performed by sequentially inserting the flexible implement into the calibration device.

Figure 14B:
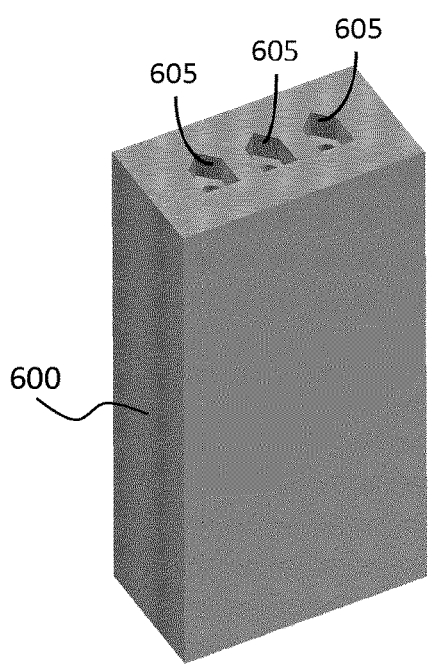
FIGS. 14B-C show views of an example calibration device for calibrating the longitudinal location of a FBG within a flexible implement.
Figure 14C:
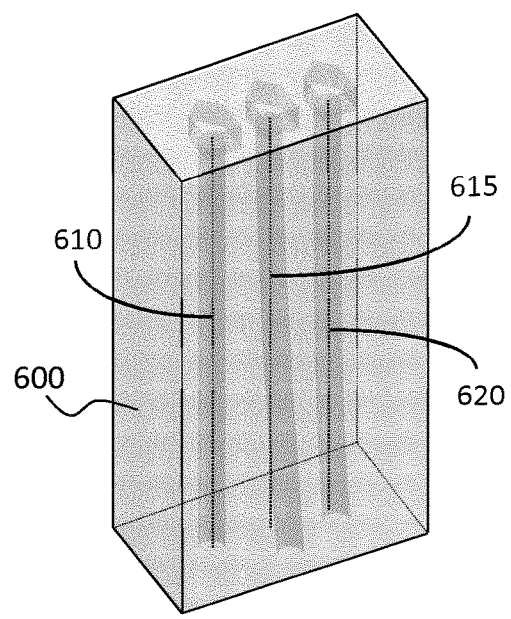

In some embodiments, the guiding features of the calibration device may be first and second channels that are configured to receive and bending the flexible implement (the flexible body portion), as illustrated in FIGS. 14B and 14C. As described in further detail below, the channels may include keyed features, such that the flexible implement is insertable into each channel in a prescribed and common angular orientation.

In another example embodiment, the guiding features may include guide posts (e.g. pairs of guide posts) extending from a substrate, where the guide posts are positioned to bend the flexible implement according to the first and second known curved profiles. In yet another alternative embodiment, the guiding features may be discrete guiding structures (e.g. pairs of posts, collars, etc.) that are robotically positionable in order to bend the flexible implement according to the first and second known curved profiles.

FIGS. 14B and 14C shows an example calibration block 600 that may be employed to bend the flexible implement according to the aforementioned method. Calibration block 600 contains three channels with different known deflection profiles 610, 615 and 620. In this case, a neutral profile 610 (i.e. no deflection) and two tip deflection profiles in common directions 615 and 620 are used as it can be seen in the semi-transparent view of the calibration block 600 in FIG. 14C.

Figure 14D:
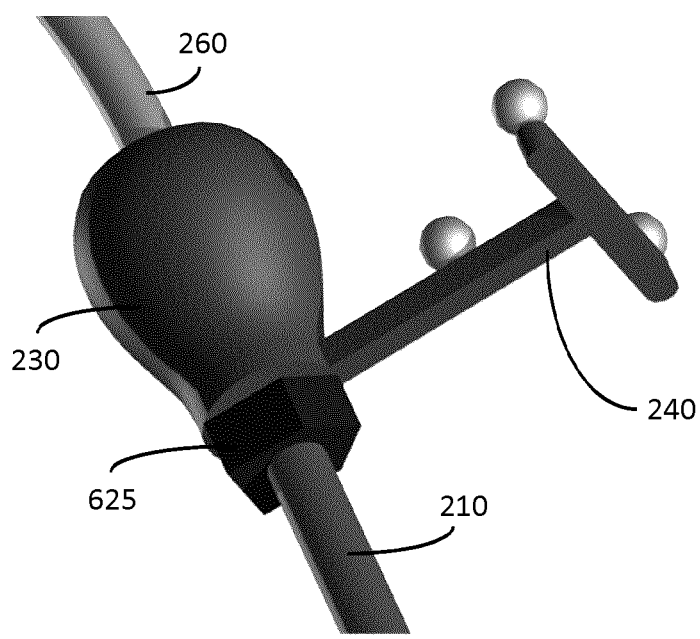
FIG. 14D shows a detailed view of an example flexible implement, showing the rigid base with a keyed feature that mates with an associated keyed feature within the calibration device.

In some embodiments, the calibration device, and the flexible implement, include keyed features that cooperatively mate, such that the flexible implement is received by the calibration device in a common angular orientation. An example implementation of such a keyed configuration is shown in FIGS. 14B to 14D, in which calibration block 600 and tracked flexible implement 200 are shown including mating keyed features (e.g. male and female) 605 and 625 respectively. The mating keyed features 605 and 625 (see FIG. 14D) ensures that tracked flexible implement 200 is only inserted in a pre-defined angular orientation into the calibration block 600, thus fixing the orientation of the marker attachment 240 to the deflection channels 610, 615 and 620.

Figure 15A:
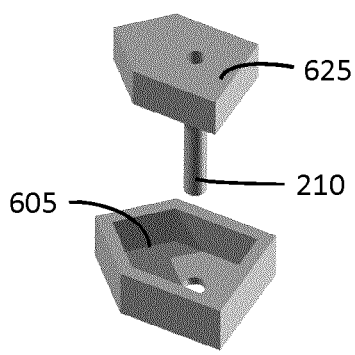
FIGS. 15A-D show various examples of keyed features for receiving the flexible implement within the calibration device in a pre-selected angular orientation.
Figure 15B:
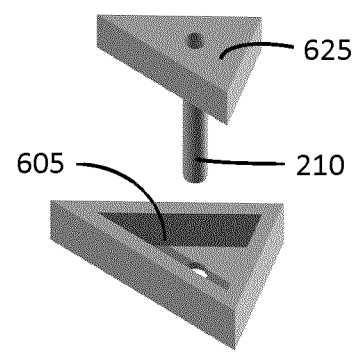
Figure 15C:
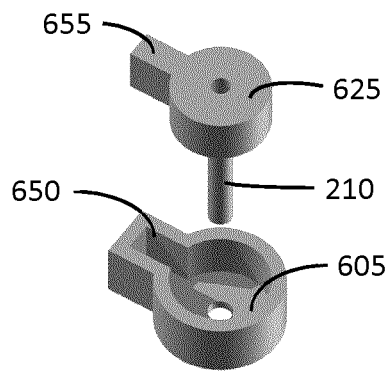
Figure 15D:
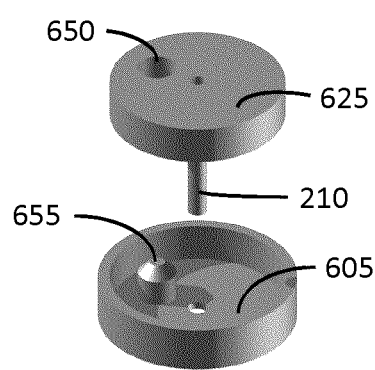

It will be understood that the keyed features shown in FIGS. 14A-C are examples of a wide variety of possible keyed features. Some non-limiting examples of alternative keyed features are shown in FIG. 15A-D. FIG. 15A shows an arrow shaped male 625 and female 605 connector, while FIG. 15B shows another example implementation involving a triangle shaped male 625 and female 605 connector. FIG. 15C illustrates an example involving a circular shaped male 625 and female 605 connector with a pin 650 and corresponding notch 655, and FIG. 15D) shows an example embodiment in which a circular shaped male 625 and female 605 connector are configured to mate via pin 650 and notch 655.

The preceding example embodiments involving calibration methods and related devices pertained to the determination of the longitudinal location of one or more FBGs. In other example embodiments presented below, methods and devices are provided for the determination of calibration parameters (e.g. coefficients of a calibration matrix) of a tracked shape sensing elongate flexible implement, where the calibration parameters relate the wavelength shift from a set of FBGs (at a common longitudinal location) to the curvature of the flexible portion of the shape sensing flexible implement.

The calibration parameters may be obtained relative to a reference frame associated with fiducial markers attached to a rigid portion of the shape sensing flexible implement. Such calibration parameters may be employed to relate measured strain-induced FBG wavelength shifts to the shape of the flexible portion of the flexible implement relative to the reference frame of the fiducial markers. When a tracking system is employed to track the position and orientation of the rigid portion of the flexible implement in a reference frame associated with the tracking system (e.g. an intraoperative reference frame associated with an operating environment), the inferred shape of the flexible portion of the flexible implement can also be determined, based on the tracked orientation of the rigid portion of the flexible implement, within the reference frame of the tracking system. This can be achieved, for example by expressing the calibration parameters within the reference frame of the tracking system (by virtue of the tracked orientation of the rigid portion of the flexible implement). The transformation effected by such calibration parameters, which relate the measured wavelength shifts and tracked orientation of the rigid portion of the flexible implement to the reference frame of the tracking system (or to another reference frame that is registered to that of the tracking system), is referred to below as an "alignment and calibration transformation".

Figure 16A:
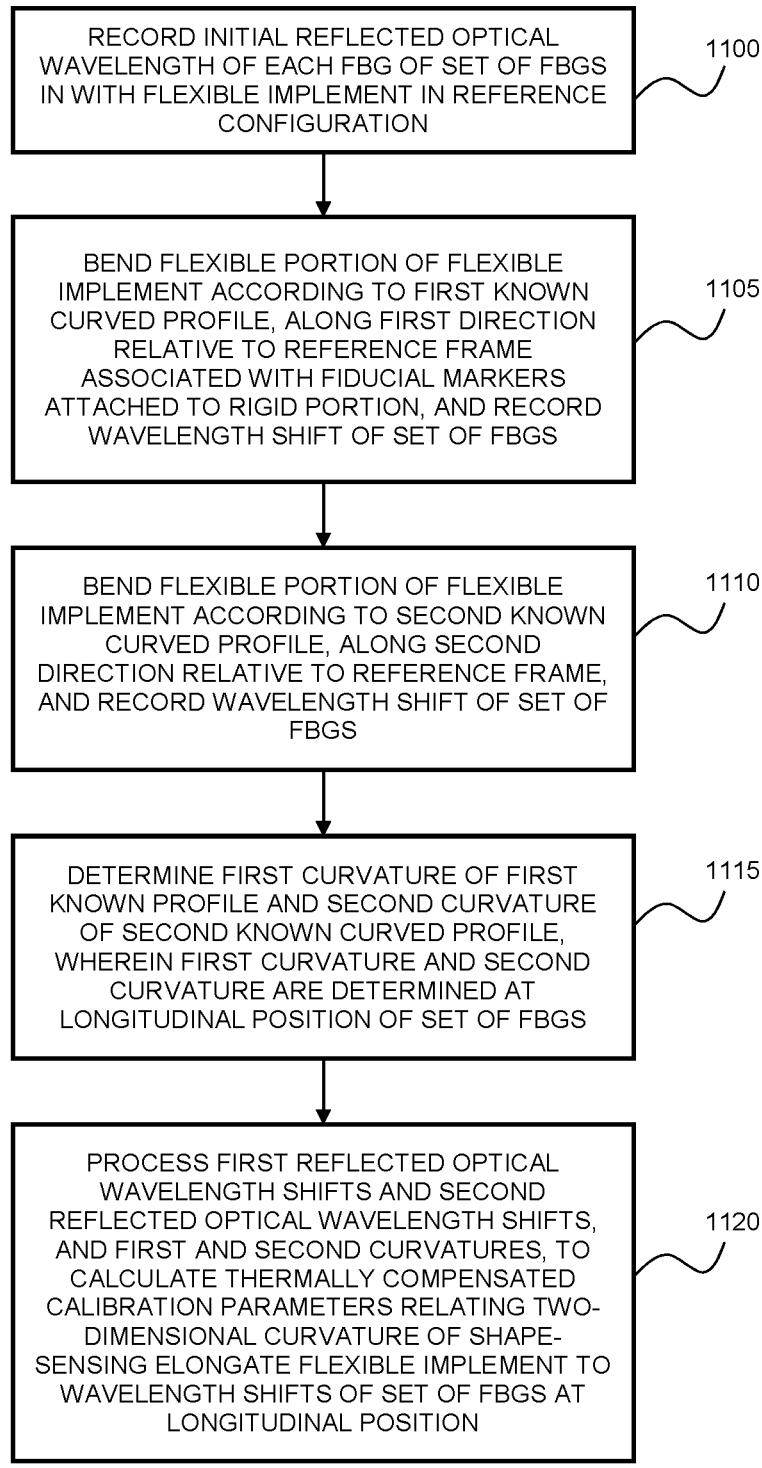
FIG. 16A is a flow chart describing an example method of determining calibration parameters that relate curvature to FBG wavelength shift for a set of FBGs of a shape-sensing flexible probe.

Referring now to FIG. 16A, a flow chart is shown that illustrates an example method of calibrating a relationship between wavelength shift and curvature for a shape-sensing elongate flexible implement, where the shape sensing element has a rigid base, to which fiducial markers are directly or indirectly attached, connected, embedded, or otherwise mechanically supported. According to the present method, calibration parameters (e.g. coefficients of a calibration matrix) are obtained for a set of FBGs located at a common longitudinal position with a flexible portion (e.g. an elongate flexible body) of the flexible implement, where the calibration parameters relate the measured wavelength shift of the FBGs to the curvature at the common longitudinal position. The shape-sensing elongate flexible implement includes at least three optical fibers, where at least two optical fibers are offset from a longitudinal axis of the shape-sensing elongate flexible implement, and where the at least three optical fibers are not mutually coplanar (thereby enabling the measurement of two-dimensional curvature that is compensated for temperature shifts). Each optical fiber includes a set of fiber Bragg gratings provided at a common longitudinal location within the shape-sensing elongate flexible implement, wherein each fiber Bragg grating of the set of fiber Bragg gratings is provided in a different optical fiber. The present may be repeated or otherwise modified in order to obtain calibration data from one or more additional sets of FBGs (at other longitudinal locations).

In step 1100, the reflected wavelengths of each FBG are recorded in a known reference configuration (e.g. in the absence of bending) of the flexible implement. For semi-rigid implements where the flexible portion is able to maintain a constant shape under its own weight (e.g. needles) an external guide may not be required to obtain the reference position data which may be straight or curved (e.g. curved biopsy needles). For a highly flexible implement not able to maintain a constant shape under its own weight (e.g. coronary catheters) a guide may be required to obtain the known reference configuration which may be a straight or curved profile. The flexible portion of the flexible implement is then bent according to a first known curved profile, in a first direction relative a reference frame associated with the fiducial markers, and the resulting wavelength shift of the FBGs is recorded, as shown at 1105. In step 1110, the flexible portion is bent according to a second known curved profile, in a second direction relative the reference frame associated with the fiducial markers, and the resulting wavelength shift of the FBGs is also recorded. In step 1115, the curvatures of the first and second known profiles are determined, based on the known shapes of the first and second curved profiles, at the common longitudinal location where the set of FBGs reside.

The recorded wavelength shifts, and the associated curvatures, are then processed, in step 1120, to determine the calibration parameters that relate wavelength shift to curvature. For example, the recorded wavelength shifts and the associated curvatures may be employed, as per equations 8 and 9, to determine the calibration parameters of a calibration matrix. While equations 8 and 9 pertain to the example case in which the first known curved profile and the second known curved profiles are orthogonal, the skilled artisan will be able adapt the equations to cases in which the first and second known profiles are directed at angles other than 90 degrees.

Also, although the preceding example method involves determining the calibration parameters within the reference frame of the fiducial markers, they may alternatively be dynamically expressed within the reference frame of the tracking system, based on the detected orientation of the fiducial markers. In other words, the tracked orientation of a fixed portion of the flexible implement may be dynamically employed to generate a dynamic calibration transformation relating the wavelength shifts of the FBGs to the orientation of the flexible portion of the flexible implement within a global static reference frame, such as the reference frame of the tracking system.

Figure 16B:
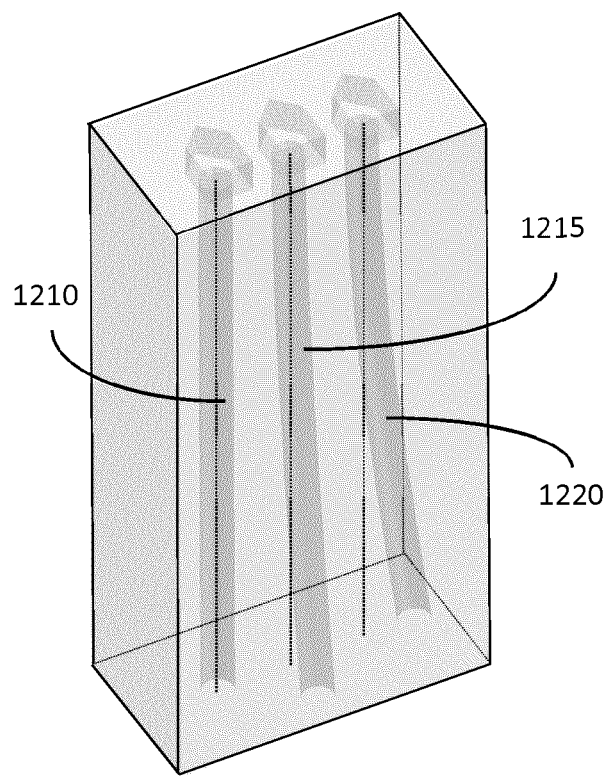
FIG. 16B shows a transparent view of an example calibration device for determining calibration parameters that relate curvature to FBG wavelength shift for a set of FBGs of a shape-sensing flexible probe.

In some example embodiments, the first and second known curved profiles may be provided by a calibration device that includes guiding features that are suitable for receiving the flexible implement and bending the flexible implement as described above. In some embodiments, the guiding features of the calibration device may be first and second channels that are configured to receive and bending the flexible implement (the flexible body portion), as illustrated in FIG. 16B. As described in further detail below, the channels may include keyed features, such that the flexible implement is insertable into each channel in a prescribed and common angular orientation.

In another example embodiment, the guiding features may include guide posts (e.g. pairs of guide posts) extending from a substrate, where the guide posts are positioned to bend the flexible implement according to the first and second known curved profiles. In yet another alternative embodiment, the guiding features may be discrete guiding structures (e.g. pairs of posts, collars, etc.) that are robotically positionable in order to bend the flexible implement according to the first and second known curved profiles.

FIG. 16B shows an example calibration block 1200 that may be employed to bend the flexible implement according to the aforementioned method. Example calibration block 1200 contains three channels with different known deflection profiles 1210, 1215 and 1220. In this case, a neutral profile 1210 (i.e. no deflection) and first and second curved deflection profiles in perpendicular directions 1215 and 1220 are used, as can be seen in the semi-transparent view of the calibration block 1200. Inserting tracked flexible implement 200 into the second deflection channel 1215 of the calibration block 1200 aligns tracked flexible implement 200 relative to the second known profile, thereby causing the corresponding deflection of the tracked flexible implement 200 (for example bending away from the fiducial markers 240 in the case shown). Although calibration block 1200 is shown including straight channel 1210, it will be understood that in other example embodiments, calibration block 1200 may include only curved channels.

Figure 16C:
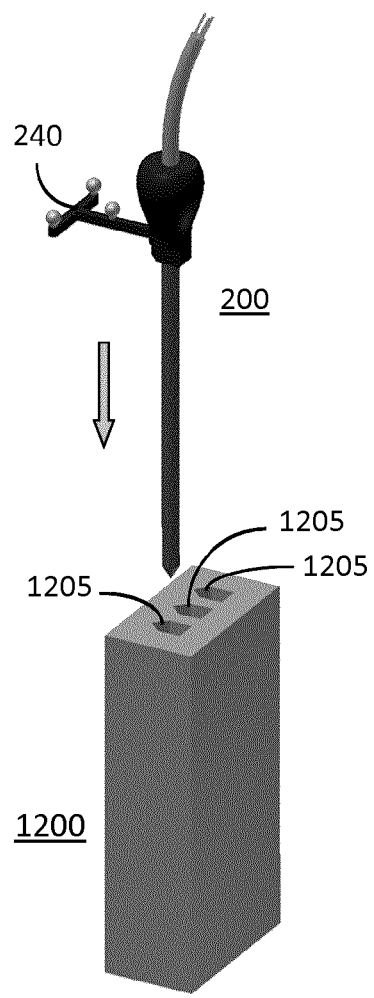
FIGS. 16C-F show views illustrating the use of an example calibration device for determining calibration parameters that relate curvature to FBG wavelength shift for a set of FBGs of a shape-sensing flexible probe.
Figure 16D:
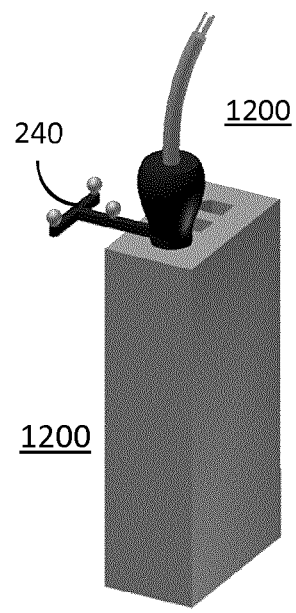
Figure 16E:
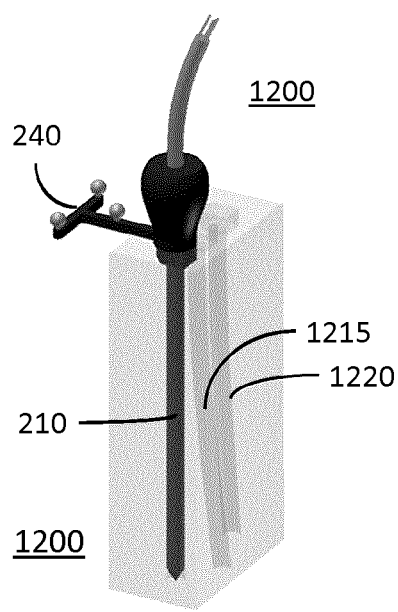
Figure 16F:
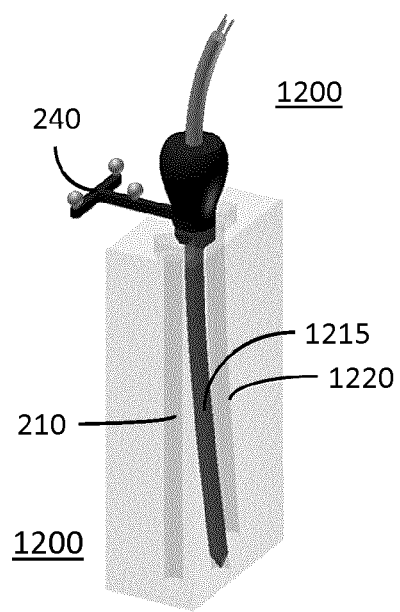

In some embodiments, the calibration device, and the flexible implement, may include keyed features that cooperatively mate, such that the flexible implement is received by the calibration device in a prescribed angular orientation, such that the flexible portion of the elongate flexible implement is bent, according to the first and second known curved profiles, in prescribed directions relative to the reference frame of the fiducial markers. Non-limiting examples of keyed features include those shown in FIGS. 14B-14D and 15A-D, as described above. It will be understood that although calibration block 1200 is shown as a single device having an integral form, in other embodiments, the calibration device may be provided as two separate components, provided that keyed features are provided for enforcing the angular orientation of the flexible implement upon insertion. FIGS. 16C-F illustrate the use of example calibration block 1200 to determine calibration parameters. In FIG. 16C, tracked flexible implement 200 is inserted into one deflection channel of the calibration block 1200. When fully inserted, keyed feature 1205 ensures a pre-defined angular orientation of the tracked flexible implement 200 relative to the calibration block 1200. As shown in FIG. 16E, calibration block may optionally include a straight channel 1200 tracked flexible implement 1200 is deflected by the known deflection profile 1210 (no deflection in the shown case) relative to the reference frame associated with fiducial markers 240. Inserting tracked flexible implement 200 into the second deflection channel 1215 of the calibration block 1200 aligns tracked flexible implement 200 relative to the second known profile, thereby causing the corresponding deflection of the tracked flexible implement 200 (for example bending away from the fiducial markers 240 in the shown case). Similarly, inserting tracked flexible implement 200 into the third deflection channel 1220 of the calibration block 1200 aligns tracked flexible implement 200 relative to the second known profile, thereby causing the corresponding deflection of the tracked flexible implement 200 (for example bending away from the fiducial markers 240 in the shown case)

In the example embodiment shown in FIGS. 16B-F, the example calibration block 1200 is shown having aligned keyed features 1205, and curved channels 1215 and 1220 are directed in different directions, such that when flexible portion 210 of elongate flexile implement 200 is inserted into the channels, flexible portion 210 is bent in different directions, as per the aforementioned method. However, in an alternative embodiment, keyed features 1205 associated with the curved channels may be oriented in different directions, while the curved channels remain aligned in a common direction, such that when flexible portion 210 of elongate flexile implement 200 is inserted into the channels, flexible portion 210 is bent in different directions.

Figure 17A:
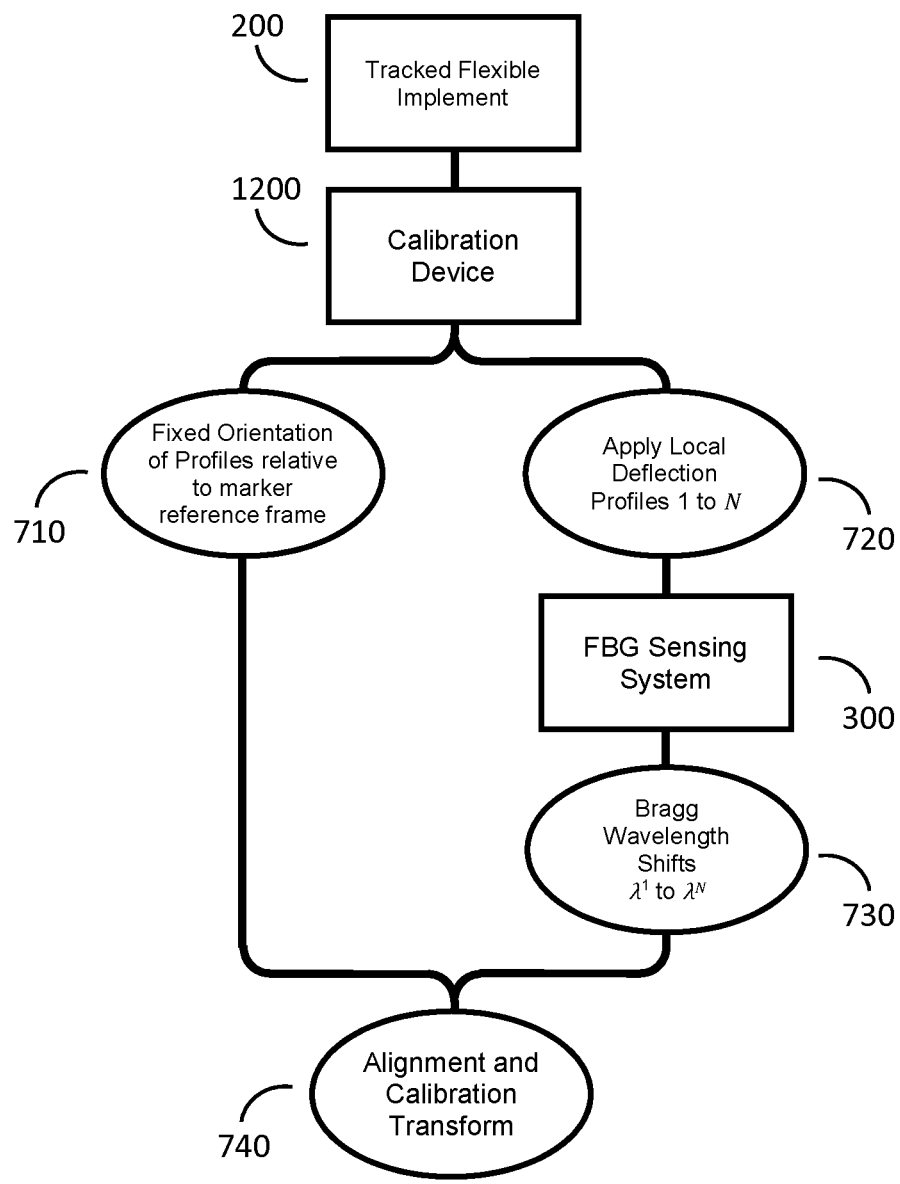
FIG. 17A shows an example flow chart for determining a calibration and alignment transformation that relates curvature to FBG wavelength shift for a set of FBGs of a shape-sensing flexible probe.

With reference to FIG. 17A, an example method is illustrated for the calibration and alignment of tracked flexible implement 200. Tracked flexible implement 200 is inserted into each of the N channels of calibration block 1200 with various known deflection profiles. The alignment mechanism of the calibration block 1200 ensures that the orientation 710 of each applied deflection profile 720 relative to the reference frame associated with fiducial markers 240 is also known. For each of the applied deflection profiles 720 i=1, 2, . . . N and each FBG 250 inside tracked flexible implement 200, the resulting Bragg wavelength shifts $\lambda^i$ 730 are measured with FBG sensing system 300. Following the steps outlined in Equations (4) to (9), the measured wavelength shifts $\lambda^i$ 730 and the known deflection profiles 720 with known orientation 710 relative to the tracking attachment 240 are used for determining the alignment and calibration transformation 740 of tracked flexible implement 200. This alignment and calibrating transformation may be dynamically generated based on the dynamically tracked orientation (determined via the tracking of the fiducial markers via a tracking system) of the rigid portion of the tracked flexible instrument to which the fiducial markers are attached.

In general, at least two channels with different detection profiles and at least two different orientations, relative to the reference frame associated with fiducial markers 240 of the tracked flexible implement 200, are required to determine the alignment and calibration transform 740. As shown in the example embodiment illustrated in FIGS. 16E-F, one of the N channels of the calibration block 1200 may have a neutral profile, which applies no deflection to tracked flexible implement 200. This allows a direct measurement of the corresponding neutral Bragg wavelengths.

In one example implementation, a user interface may be employed to guide the user through the calibration process. For example, a user interface may be employed to query the user to insert tracked flexible implement 200 into specific channels inside the calibration block 1200 (marked with numbers or otherwise) and to confirm when the insertion is done.

In some embodiments, calibration information, such as calibration parameters that relate the measured strain-induced FBG wavelength shifts to the shape of the flexible portion of the flexible implement relative to the reference frame of the fiducial markers, are stored such that they may be retrieved and employed to determine the orientation of the flexible portion of the tracked flexible implement within the reference frame of the tracking system. For example, calibration information may be stored within a computing system (e.g. control and processing unit 10).

Alternatively, calibration information may be stored externally. For example, calibration information may be provided on or stored within the tracked flexible implement, such that the calibration information may be obtained from the tracked flexible implement. For example, calibration information may be stored within a local memory device housed within tracked flexible implement, such that the memory device may be interrogated (e.g. via a wired or wireless connection) to obtain the calibration information. In another example implementation, the calibration information may be stored in another computer-readable format, such as an optical bar code (e.g. a 2D bar code) or a RFID device.

In some example embodiments, the fiducial markers may be permanently affixed to the flexible implement, and the calibration device may be employed, after fixation of the fiducial markers, to obtain the calibration information relating the measured strain-induced FBG wavelength shifts to the shape of the flexible portion of the flexible implement relative to the reference frame of the fiducial markers. This process may be performed one or more times, for example, to correct for long-term drift in the relative position of the fiducial markers relative to the flexible implement. The calibration information may be stored as described above.

In some example implementations, a fiducial marker assembly (which may optionally include a handheld body, as noted below) may be removably attachable to the flexible implement. In such a case, the fiducial marker assembly need not be precisely aligned with the flexible implement, and the calibration methods and devices described herein may be employed to calibrate for the relative alignment between the reference frame of the fiducial markers and apparatus. The flexible implement may be disposable, and the fiducial marker assembly may be re-used one or more times. For example, the fiducial markers may be removably attached to the flexible portion using a removably attachable marker assembly based on the embodiments shown in PCT Patent Publication No. WO 2014/005225, titled "ATTACHMENTS FOR TRACKING HANDHELD IMPLEMENTS", which is incorporated herein by reference in its entirety.

Figure 17B:
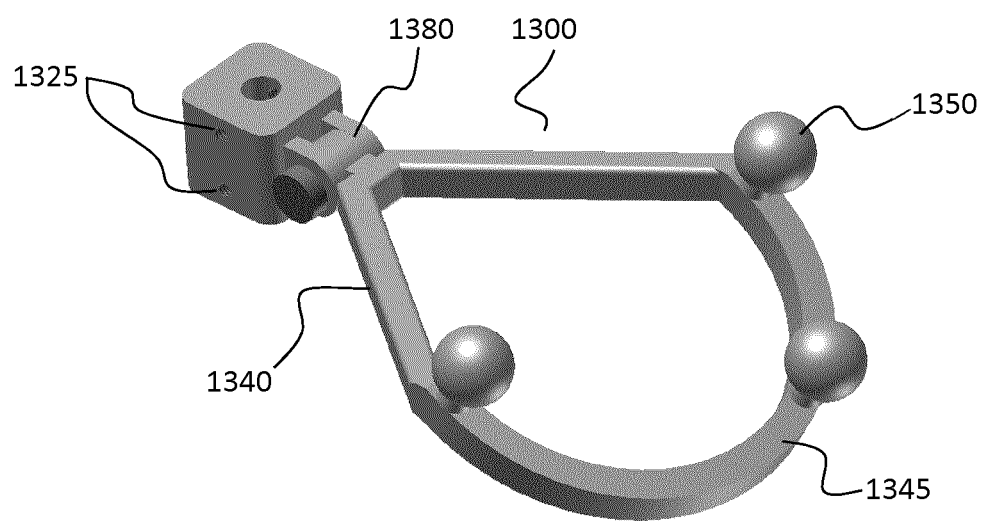
FIGS. 17B-C show non-limiting examples of marker assemblies that may be removably attachable to a shape-sensing flexible implement.
Figure 17C:
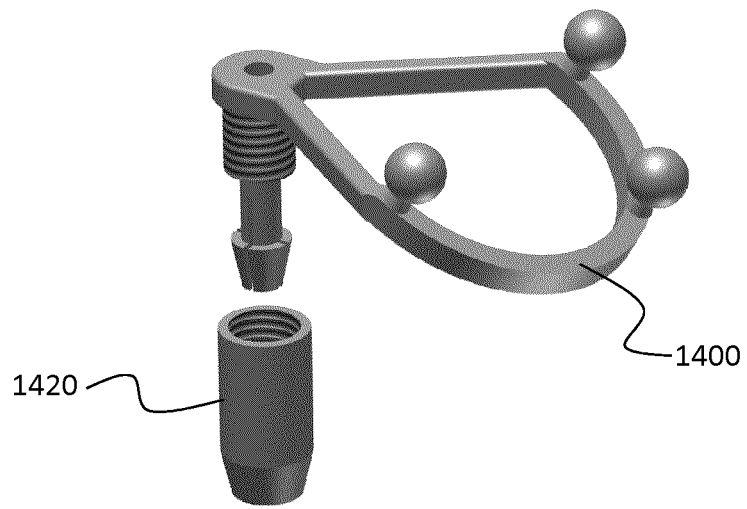

Non-limiting examples of removably attachable fiducial marker assemblies are shown in FIGS. 17B and 17C. In the example embodiment shown in FIG. 17B, example marker assembly 1300 includes a support member (1340, 1345) for supporting fiducial markers 1350, which are aligned in a plane defined by distal arc 1345. In this example, the shaft of the flexible implement is inserted through a hole in connector 1320. Set screws 1325 secure marker assembly 1300 to the flexible implement, preventing sliding and rotation of the marker assembly 1300. As shown in FIG. 17A, a hinge joint 1380 may be employed to vary the angular orientation of marker assembly 1300, which allows the user to select an arbitrary angle of the fiducial marker assembly. After fixing the angle (e.g. with a fixation screw), the calibration information may be determined, using the methods described above. FIG. 17C shows an example implementation in which fiducial marker assembly 1400 is configured to mate with a handle body 1420 and clamp onto the flexible implement.

In one example embodiments, the calibration device may include fiducial markers that allow for the determination of the orientation of the calibration device within the reference frame of a tracking system. This allows the tracking system determine, within the tracked reference frame, the orientation of the inserted tracked flexible implement relative the calibration device and therefore an automatic identification of the deflection channel into which the tracked flexible implement is inserted during a step of the calibration method.

In one example embodiment, a single feature or set of features for bending the flexible portion of the tracked flexible implement may be employed to bend the tracked flexible implement according to the first and second known curved profiles, where the steps of bending the flexible portion along the first and second known curved profiles are achieved by rotating the tracked flexible implement relative to the calibration device. Both the tracked flexible implement and the calibration device include fiducial markers, thereby enabling the determination of the orientation of the tracked flexible implement relative to the calibration device. Accordingly, the flexible portion of the tracked flexible implement may be initially bent according to a first known curved profile by inserting the tracked flexible implement into the guiding features in a first angular orientation, where this orientation is determined by the tracking system, and then rotating the tracked flexible implement into a second angular orientation, which establishes the second known curved profile, where the second angular orientation is also determined by the tracking system. According to such an embodiment, a single known curved profile is established by the guiding features of the calibration device, while the direction of the bending of the tracked flexible implement is varied between first and second directions by rotating the tracked flexible implement into two distinct orientations (which are measured by the tracking system).

FIGS. 18A and 18B illustrate an example implementation of a calibration block 800, which can be employed for the calibration and alignment of tracked flexible implement 200, according to the aforementioned method involving tracked rotation of the tracked flexible implement. Example calibration block 800 contains two channels: neutral deflection profile 805 (i.e. no deflection) and one tip deflection profile 810, where the two channels can be seen in the semi-transparent view shown in FIG. 18B. Fiducial markers 820 allow tracking system 130 to track position and orientation of calibration block 800, such that orientation of the tracked flexible implement can be measured for the determination of the directions of the first and second known curved profiles along which the tracked flexible implement is bent. As noted above, it will be understood that example calibration block 800 need not include the straight channel, and that the unbent measurement may be made in the absence of the calibration device, or using a separate calibration device with guiding features for receiving the tracked flexible implement in an undeflected state.

Figure 19A:
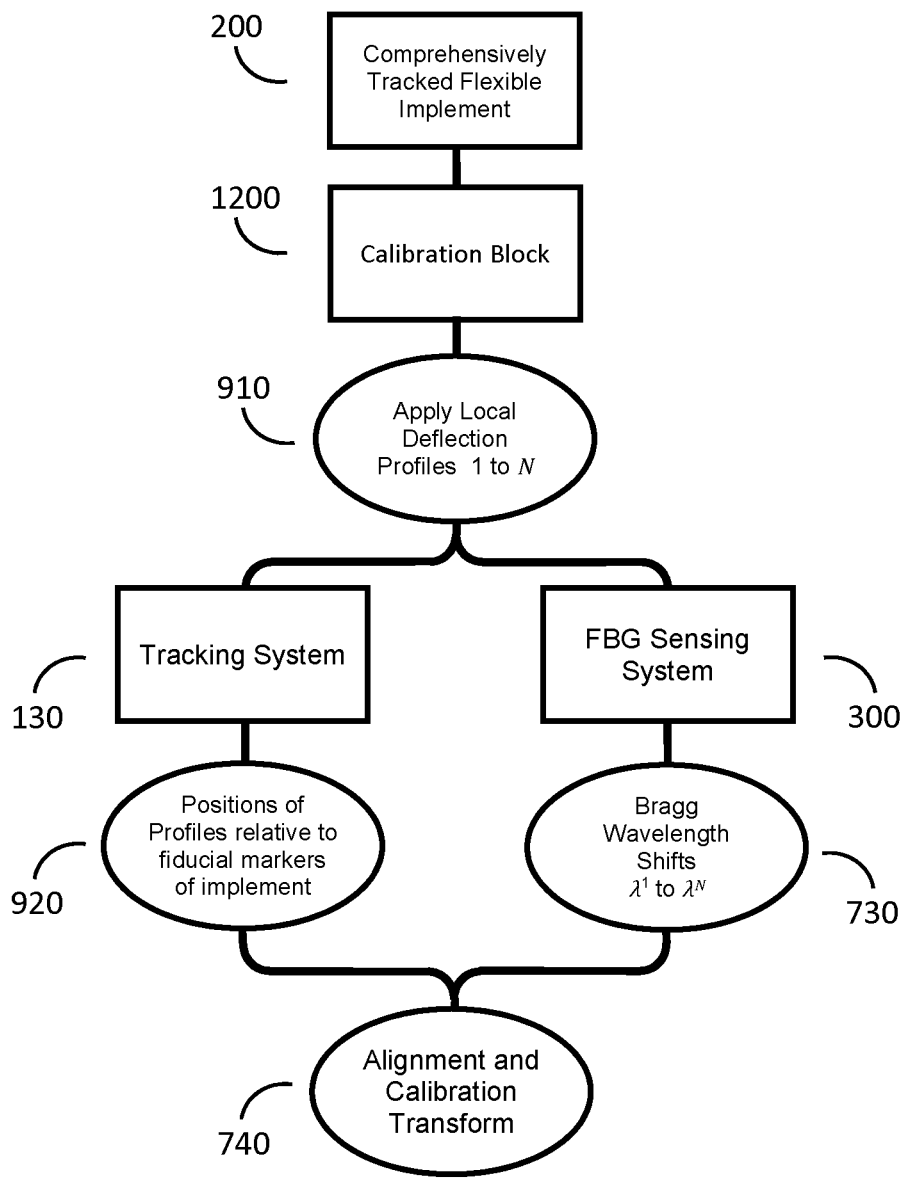
FIG. 19A is a flow chart illustrating an example method of obtaining calibration parameters for a tracked flexible probe, in which the orientation of the tracked flexible probe relative to a calibration device is determined using a tracking system that detects fiducial markers associated with both the tracked flexible implement and the calibration device.
Figure 20A:
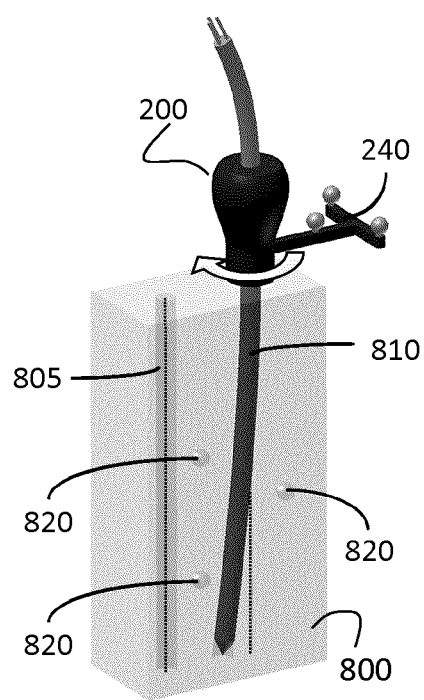
FIGS. 20A-B illustrate the rotation of a tracked flexible implement within a single channel of a calibration device in order to orient the tracked flexible implement in two different configurations when performing a calibration method.
Figure 20B:
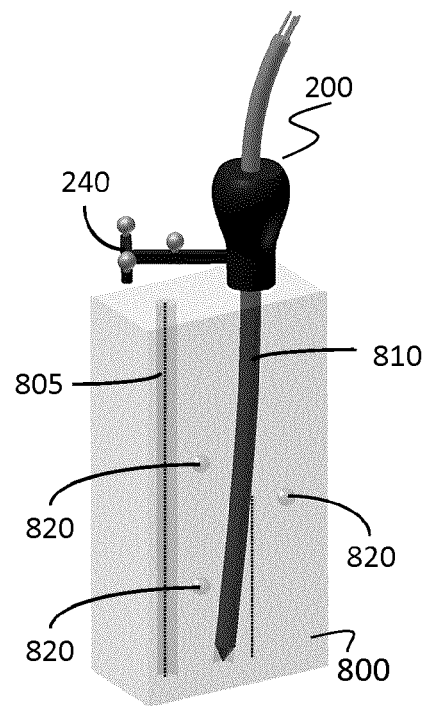

An example flow chart 900 for the calibration and alignment of tracked flexible implement 200 using calibration block 800 is shown in FIG. 19A. When inserted into the deflection channel 810 of the calibration block 800, the tracked flexible implement 200 is deflected by the known deflection profile as shown in FIG. 20A. The user then rotates the inserted flexible implement 200 inside the calibration block 800 (optionally under the guidance of a user interface, as described above), such that deflection profile 810 is applied with different orientations relative to the tracking attachment 240 (for example new orientation shown in FIG. 20B. During the rotation, optical tracking system 130 detects the relative position and orientation the calibration block 800 and the tracked flexible implement 200, which allows the determination of the orientation 920 of the deflection profile 810 relative to the fiducial markers of the inserted tracked flexible implement 200. FBG sensing system 300 measures the corresponding Bragg wavelength shifts $\lambda^i$ 930 for each FBG inside tracked flexible implement 200. Following the steps outlined in Equations (4) to (9), the known deflection profiles with known orientations relative to the reference frame of the fiducial markers of the tracked flexible implement and the corresponding wavelength shifts $\lambda^i$ 730 and are used for determining the calibration parameters that relate the local curvature at the FBG location to the measured wavelength shifts. As noted above, the calibration parameters can be expressed within the local reference frame of the tracked flexible implement 200, or may be expressed within the reference frame of the tracking system, thereby providing the alignment and calibration transformation.

In an example implementation of the calibration procedure shown in FIG. 19A, the tracked flexible implement may be fully inserted into the calibration block 800 during rotation. A fastening mechanism between the flexible implement 200 and the calibration block 800 can be used to ensure full insertion during the rotation. An example of a keyed feature pair which incorporates a fastening mechanism is shown in FIGS. 19B-19D at various stages of mating. The mechanism shown is based on a ball pin lock. Alternatively, the information from the tracking system 130 can be used to determine the insertion depth of the flexible implement 200 into the calibration block 800.

Figure 21A:
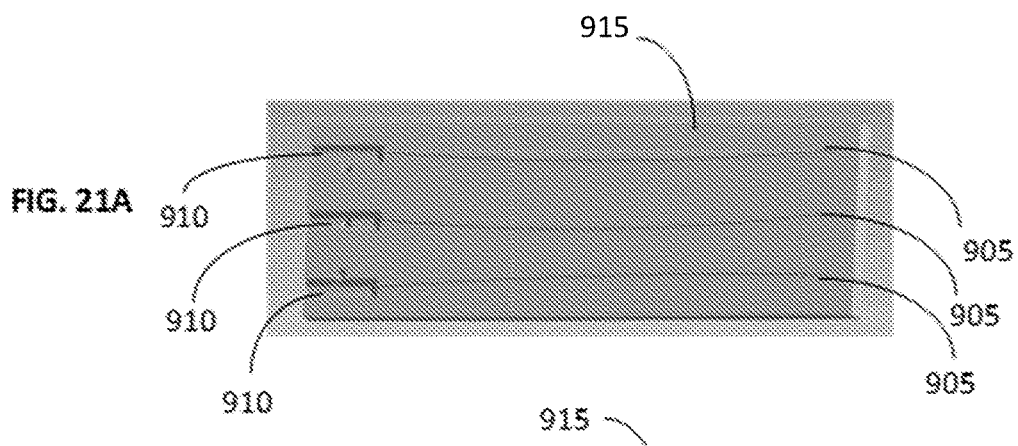
FIGS. 21A-C illustrate various examples of calibration devices that employ different types of guiding features for bending the tracked flexible implement according to known curved profiles.
Figure 21B:
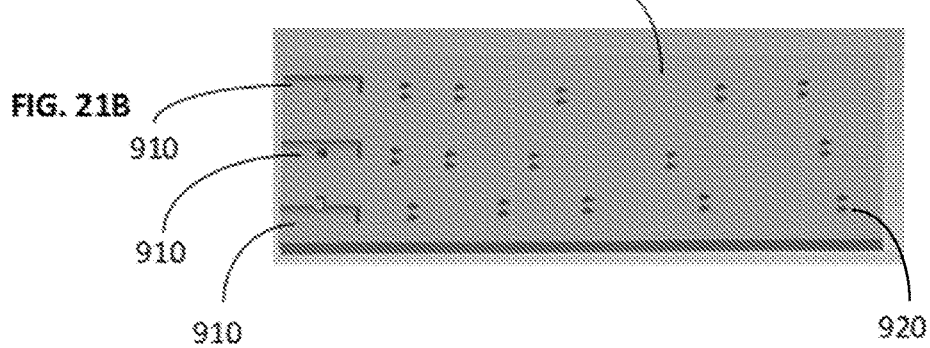
Figure 21C:
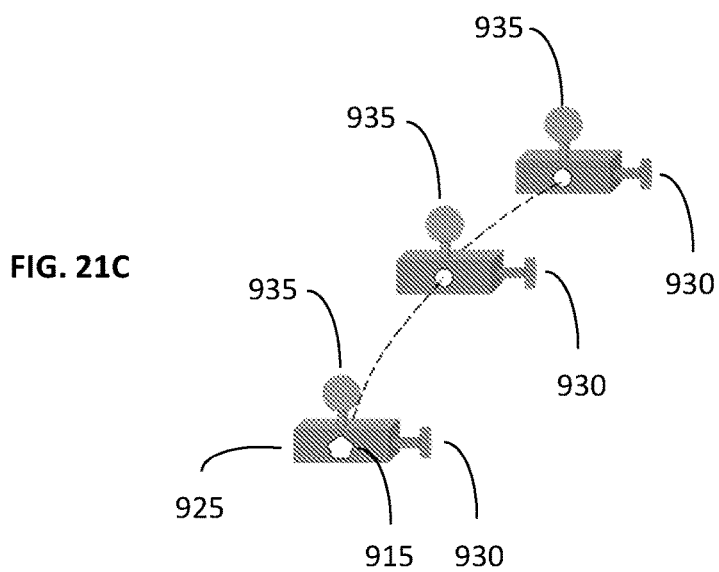

In another example implementation, a calibration device similar to that shown in FIGS. 18A and 18B may be provided, where the calibration device includes a channel, similar to channel 810, which can be employed to bend the flexible portion of the tracked flexible probe according to the first and second known curved profiles by rotating the tracked flexible implement within the channel, but where the calibration device includes two keyed features that require that the flexible tracking device be received in one of two possible configurations upon insertion. Example of such key features are shown in FIGS. 18C and 18D which utilize degenerate pins 650 or notches 655. Such an embodiment would not require the inclusion of fiducial markers, and would not rely on the tracking system to measure the relative orientation between the tracked flexible implement and the calibration device. In many of the calibration methods described above, the flexible implement is bent according to known curved profiles. Although many of the preceding example embodiments describe the use of calibration devices with channels to impose the deflection profiles, it will be understood that guiding features other than channels may be employed to bend the flexible implement. FIGS. 21A-C show three example variations for applying a known deflection profile to the flexible implement.

FIG. 21A demonstrates an example calibration device in which the flexible implement is placed within channels 905 engraved into a plate 915. An adapter 910 for accepting the tracking attachment in a pre-defined orientation is located along the trajectory. This calibration device may be directly embedded within the packaging of the flexible implement typically associated with medical catheters. This can be accomplished by using injection molding processes to embed the key features and channels directly into plastic packaging (trays and covers).

FIG. 21B demonstrates another example calibration device in which pegs 920 are held on plate 915 are used to channel the flexible implement along a pre-defined trajectory. As above, an adapter 910 to accept the tracking attachment is shown. This calibration device could be readily incorporated into the packaging of the flexible implement.

FIG. 21C demonstrates a third example calibration device in which blocks 925 are attached to the flexible implement and secured using thumbscrews 930. Each of the blocks incorporate a tracking marker 935 with the first block 925 also having an adapter 915 to accept the tracking frame in a pre-defined orientation. The marker on each block 925 can be tracked by a tracking system to define the deflection profile in real time for calibration.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1. Park, Yong-Lae, et al. "Real-time estimation of 3-D needle shape and deflection for MRI-guided interventions." Mechatronics, IEEE/ASME Transactions on 15.6 (2010): 906-915.
2. Kersey, Alan D., et al. "Fiber grating sensors." Journal of lightwave technology 15.8 (1997): 1442-1463.

Therefore what is claimed is:

1. A method of determining a longitudinal location of a fiber Bragg grating within an optical fiber, wherein the optical fiber is attached to or housed within an elongate flexible implement, the method comprising:
   recording an initial reflected optical wavelength of the fiber Bragg grating in the absence of bending of the elongate flexible implement;
   providing a calibration device comprising:
      one or more first guiding features suitable for receiving the elongate flexible implement and bending the elongate flexible implement along a first known curved profile; and
      one or more second guiding features suitable for receiving the elongate flexible implement and bending the elongate flexible implement along a second known curved profile;
      wherein said first and second guiding features are configured such that a ratio of the curvature of the first known curved profile to the curvature of the second known curved profile, as determined at a common longitudinal distance along each known curved profile, varies with longitudinal distance;
      wherein said first and second guiding features are configured to bend the elongate flexible implement along a common direction; and
      wherein the first known curved profile and the second known curved profile are selected such that a dependence, on longitudinal distance, of the ratio of the curvature of the first known curved profile to the curvature of the second known curved profile, is single-valued;
   inserting the elongate flexible implement into the first guiding feature such that the elongate flexible implement is bent according to the first known curved profile and recording a first reflected optical wavelength shift of the fiber Bragg grating;
   inserting the elongate flexible implement into the second guiding feature such that the elongate flexible implement is bent according to the second known curved profile and recording a second reflected optical wavelength shift of the fiber Bragg grating; and
   determining, as the longitudinal location of the fiber Bragg grating, a longitudinal distance for which a ratio of the curvature of the first known curved profile to the curvature of the second known curved profile equals a ratio of the first reflected optical wavelength shift to the second reflected optical wavelength shift.

2. The method according to claim 1 wherein the calibration device is keyed to corresponding features of the elongate flexible implement, such that the elongate flexible implement is bent according to the first known curved profile and the second known curved profile in a common angular orientation relative to a rotational axis of the elongate flexible implement.

3. The method according to claim 1 wherein the guiding features comprise a first curved channel configured to bend the elongate flexible implement according to the first known curved profile, and a second curved channel configured to bend the elongate flexible implement according to the second known curved profile.

4. The method according to claim 3 wherein each channel of the calibration device is keyed to a corresponding feature of the elongate flexible implement, such that the elongate flexible implement is inserted into each channel in a common angular orientation relative to a rotational axis of the elongate flexible implement.

5. The method according to claim 1 wherein the guiding features comprise a first set of discrete of guide posts configured to bend the elongate flexible implement according to the first known curved profile, and a second set of discrete of guide posts configured to bend the elongate flexible implement according to the second known curved profile.

6. The method according to claim 1 wherein the first known curved profile and the second known curved profile are polynomials having different degrees, wherein the degree of each known curved profile is at least two.

7. A calibration apparatus for use in determining a longitudinal location of a fiber Bragg grating within an optical fiber, wherein the optical fiber is attached to or housed within an elongate flexible implement, the calibration apparatus comprising:
   one or more first guiding features suitable for receiving the elongate flexible implement and bending the elongate flexible implement along a first known curved profile; and
   one or more second guiding features suitable for receiving the elongate flexible implement and bending the elongate flexible implement along a second known curved profile;
   wherein said first and second guiding features are configured such that a ratio of the curvature of the first known curved profile to the curvature of the second known curved profile, as determined at a common longitudinal distance along each known curved profile, varies with longitudinal distance;
   wherein said first and second guiding features are configured to bend the elongate flexible implement along a common direction; and
   wherein the first known curved profile and the second known curved profile are selected such that a dependence, on longitudinal distance, of the ratio of the curvature of the first known curved profile to the curvature of the second known curved profile, is single-valued.

8. The calibration apparatus according to claim 7 wherein said first and second guiding features comprise:

a first curved channel configured to bend the elongate flexible implement according to the first known curved profile; and a second curved channel configured to bend the elongate flexible implement according to the second known curved profile.

9. The calibration apparatus according to claim 8 wherein each channel is keyed to a corresponding feature on the elongate flexible implement, such that the elongate flexible implement is inserted into each channel in a common angular orientation relative to a rotational axis of the elongate flexible implement.

10. The calibration apparatus according to claim 7 wherein said first and second guiding features comprise:

a first set of discrete of guide posts configured to bend the elongate flexible implement according to the first known curved profile; and a second set of discrete of guide posts configured to bend the elongate flexible implement according to the second known curved profile.

11. The calibration apparatus according to claim 7 wherein the first known curved profile and the second known curved profile are polynomials having different degrees, wherein the degree of each known curved profile is at least two.

12. The calibration apparatus according to claim 7 further comprising one or more additional guiding features that are configured to receive the elongate flexible implement without bending the elongate flexible implement.

\* \* \* \* \*